(12) United States Patent
Lambarth et al.

(10) Patent No.: US 12,263,100 B2
(45) Date of Patent: Apr. 1, 2025

(54) BONE FRAGMENT COLLECTOR AND PROCESSOR

(71) Applicant: Stryker Corporation, Kalamazoo, MI (US)

(72) Inventors: Clifford Edwin Lambarth, Portage, MI (US); Jason James Wroblewski, Portage, MI (US); Robin Beverly Wynne Babaris, Portage, MI (US); Dennis Alan Stratton, Plainwell, MI (US)

(73) Assignee: Stryker Corporation, Portage, MI (US)

(*) Notice: Subject to any disclaimer, the term of this patent is extended or adjusted under 35 U.S.C. 154(b) by 1176 days.

(21) Appl. No.: 17/046,407

(22) PCT Filed: Apr. 16, 2019

(86) PCT No.: PCT/US2019/027621
§ 371 (c)(1),
(2) Date: Oct. 9, 2020

(87) PCT Pub. No.: WO2019/204268
PCT Pub. Date: Oct. 24, 2019

(65) Prior Publication Data
US 2021/0113351 A1   Apr. 22, 2021

Related U.S. Application Data

(60) Provisional application No. 62/658,421, filed on Apr. 16, 2018.

(51) Int. Cl.
*A61F 2/46* (2006.01)

(52) U.S. Cl.
CPC .... *A61F 2/4644* (2013.01); *A61F 2002/4645* (2013.01)

(58) Field of Classification Search
CPC ........ A61M 1/79; A61M 5/3145; A61M 5/38; A61M 2005/1657; A61C 17/065; A61F 2/4644; A61F 2002/4645
See application file for complete search history.

(56) References Cited

U.S. PATENT DOCUMENTS

| 5,954,961 A | 9/1999 | Carchidi |
| 6,387,070 B1 | 5/2002 | Marino et al. |

(Continued)

FOREIGN PATENT DOCUMENTS

| CN | 1819849 A | 8/2006 |
| CN | 102260628 A | 11/2011 |

(Continued)

OTHER PUBLICATIONS

International Search Report for Application No. PCT/US2019/027621 dated Aug. 2, 2019, 5 pages.

(Continued)

*Primary Examiner* — Anu Ramana
(74) *Attorney, Agent, or Firm* — Howard & Howard Attorneys PLLC

(57) ABSTRACT

A device (10) for collecting and processing bone fragments is disclosed. The device comprises a chamber member (12), a press member (14), an intake port (16), and a vacuum port (18). A compression surface (20) and a filter support surface (22) configured to support a filter are defined by said chamber and/or press member. The intake port is on the chamber and/or press member and is configured to receive a composition comprising bone fragments. The vacuum port is on the chamber and/or press member. The chamber member and the press member are rotationally coupled with one another. The composition is acquired through the intake port and collected between the compression surface and the filter support surface. The application of rotational force to the chamber and/or press member in a first direction moves (Continued)

the compression surface and the filter support surface together to compress the composition therebetween to compact, and further remove filtrate from the composition.

19 Claims, 15 Drawing Sheets

(56) References Cited

U.S. PATENT DOCUMENTS

| | | |
|---|---|---|
| 7,214,059 B2 | 5/2007 | Takahashi |
| 7,621,917 B2 | 11/2009 | Geneve et al. |
| 7,758,556 B2 | 7/2010 | Perez-Cruet et al. |
| 7,971,728 B2 | 7/2011 | Anspach et al. |
| 8,043,291 B2 | 10/2011 | Accordino |
| 8,632,242 B2 | 1/2014 | Hoerger et al. |
| 8,740,908 B2 | 6/2014 | Farley et al. |
| 8,845,605 B2 * | 9/2014 | Hensler .................. A61M 1/60 604/319 |
| 8,920,393 B2 | 12/2014 | Hensler et al. |
| 9,358,327 B1 | 6/2016 | Venturi |
| 9,763,774 B2 * | 9/2017 | Chen .................. A61F 2/1678 |
| 9,872,944 B1 * | 1/2018 | Willard .............. A61B 10/0045 |
| 10,064,984 B2 | 9/2018 | Locke et al. |
| 10,195,320 B2 * | 2/2019 | Fisher .................. A61M 1/79 |
| 10,940,247 B2 * | 3/2021 | Willard ................ A61M 1/631 |
| 11,337,710 B2 * | 5/2022 | Assell .................... A61M 1/79 |
| 2004/0026341 A1 | 2/2004 | Hogberg et al. |
| 2006/0052760 A1 | 3/2006 | Batzdorf |
| 2007/0225665 A1 | 9/2007 | Perez-Cruet et al. |
| 2011/0301496 A1 | 12/2011 | Lampropoulos et al. |
| 2012/0109227 A1 | 5/2012 | Farley et al. |
| 2012/0279933 A1 | 11/2012 | Hensler et al. |
| 2014/0358080 A1 | 12/2014 | Bryan |
| 2015/0335785 A1 | 11/2015 | Ayers |
| 2016/0325018 A1 | 11/2016 | Assell et al. |
| 2017/0202579 A1 | 7/2017 | Abrahams et al. |

FOREIGN PATENT DOCUMENTS

| | | |
|---|---|---|
| CN | 104144719 A | 11/2014 |
| CN | 104884101 A | 9/2015 |
| CN | 104968303 A | 10/2015 |
| CN | 206730662 U | 12/2017 |
| WO | 2014126554 A1 | 8/2014 |
| WO | 2017066720 A1 | 4/2017 |

OTHER PUBLICATIONS

English language abstract for CN 104144719 A extracted from espacenet.com database on Nov. 7, 2023, 1 page.

English language abstract and machine-assisted English translation for CN 206730662 U extracted from espacenet.com database on Nov. 7, 2023, 7 pages.

English language abstract for CN 1819849 A extracted from espacenet.com database on Aug. 14, 2024, 2 pages.

English language abstract for CN 102260628 A extracted from espacenet.com database on Aug. 14, 2024, 2 pages.

English language abstract for CN 104884101 A extracted from espacenet.com database on Aug. 14, 2024, 2 pages.

English language abstract for CN 104968303 A extracted from espacenet.com database on Aug. 14, 2024, 2 pages.

* cited by examiner

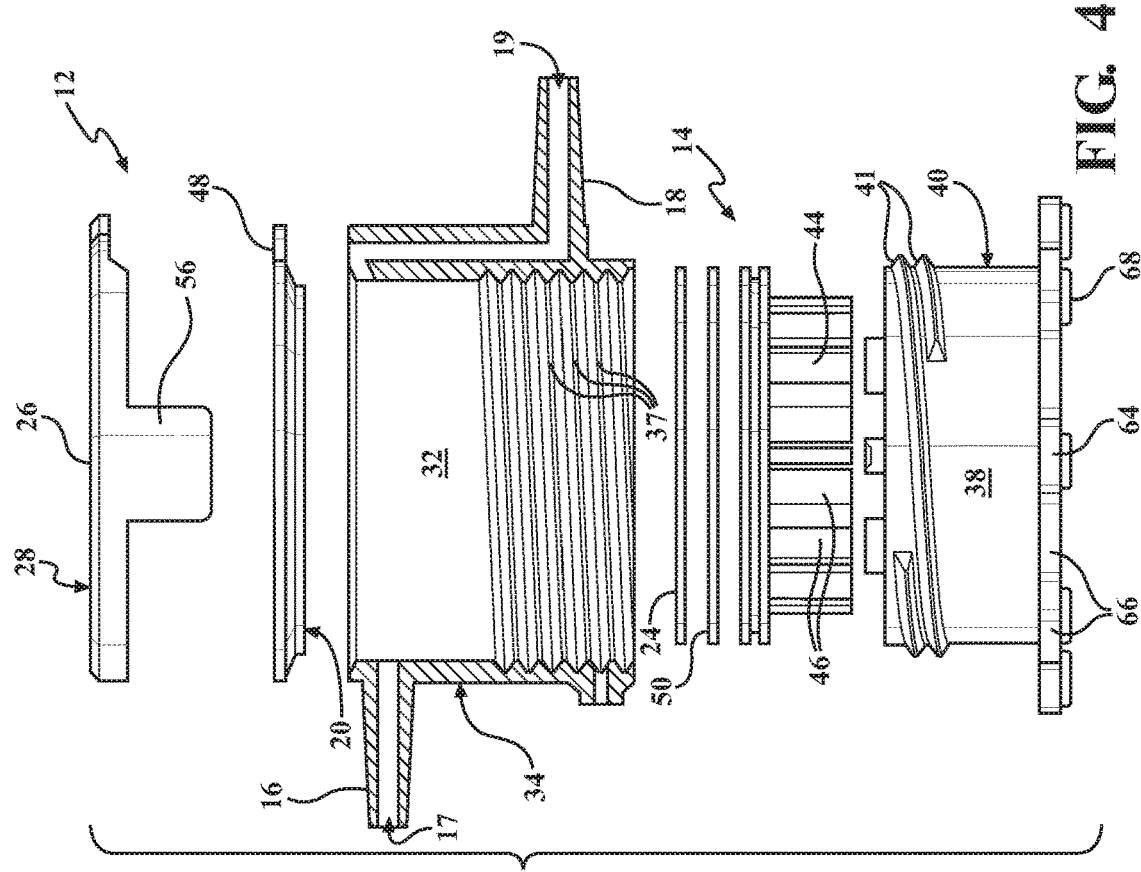
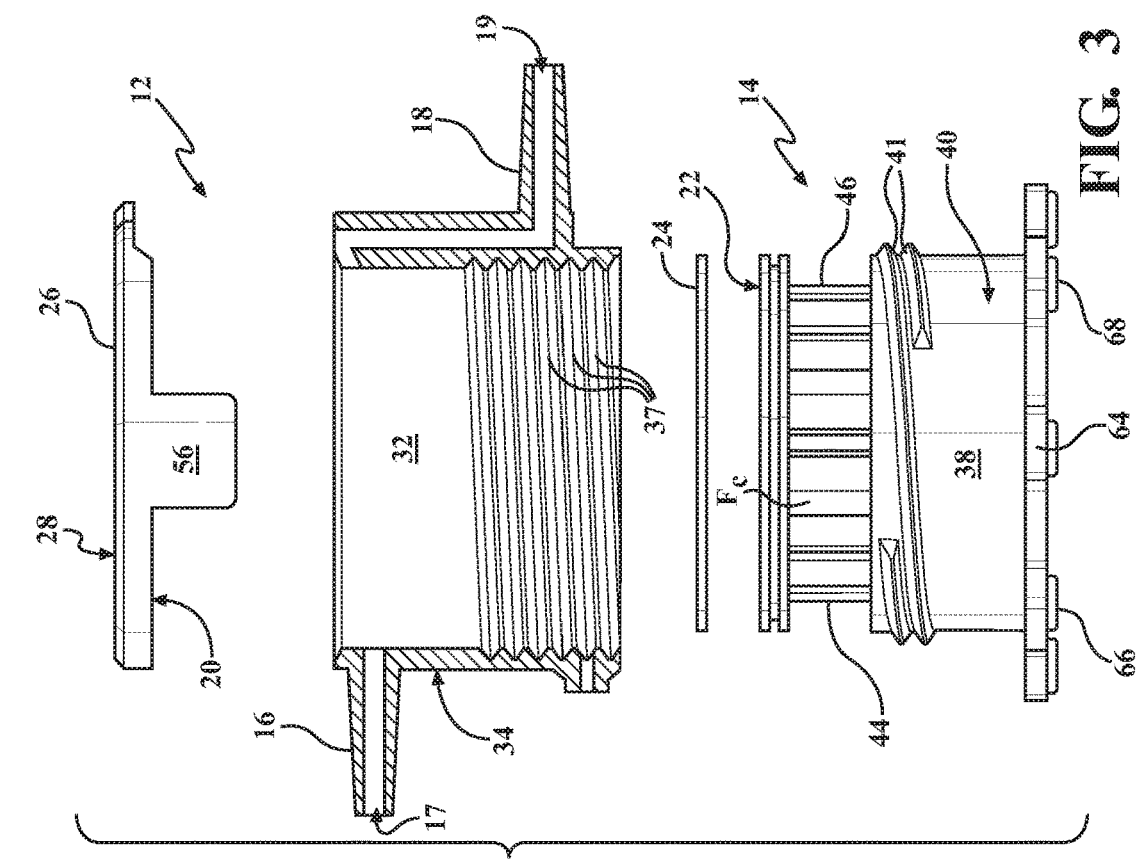

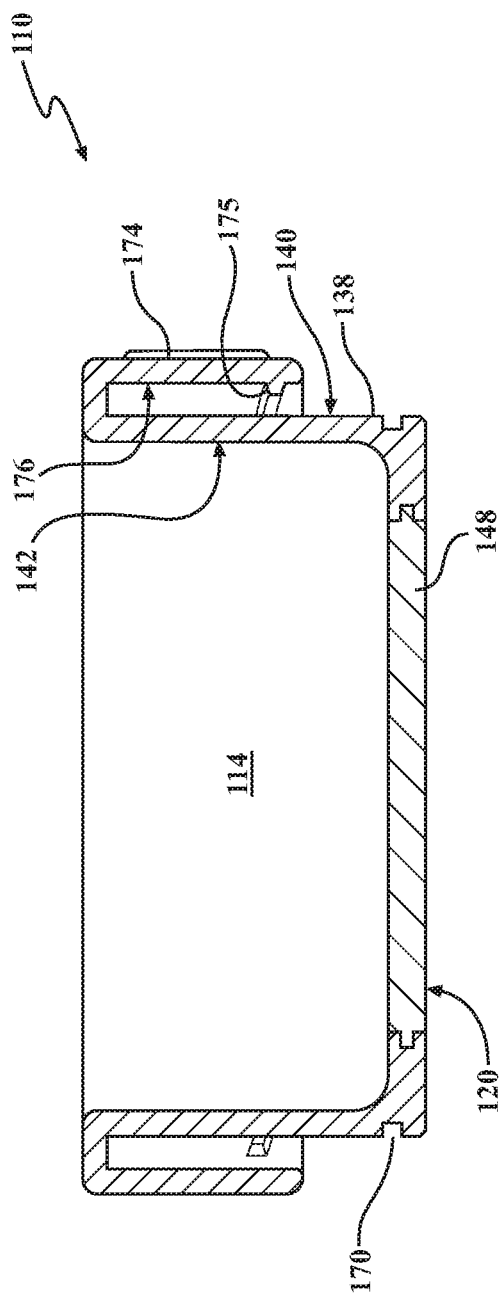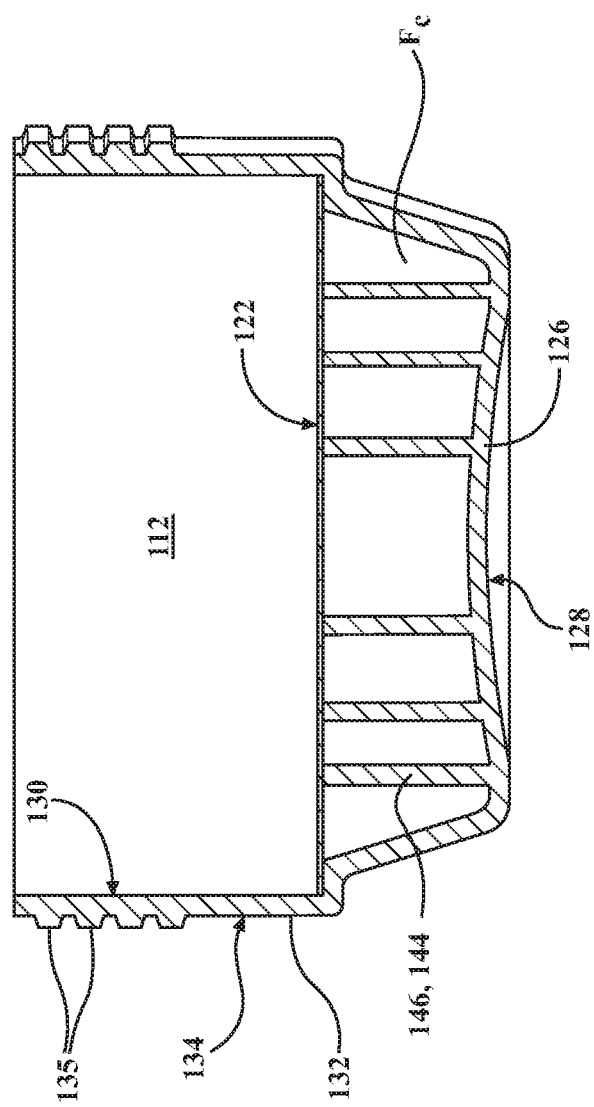
FIG. 14

BONE FRAGMENT COLLECTOR AND PROCESSOR

CROSS-REFERENCE TO RELATED APPLICATIONS

This application is the National Stage of International Application No. PCT/US2019/027621, filed on Apr. 16, 2019, which claims the benefit of U.S. Provisional Application 62/658,421, filed on Apr. 16, 2018. The entire contents of these applications are incorporated herein by reference in their entirety.

BACKGROUND

Conventional medical and surgical procedures routinely involve the use of systems and tools which allow surgeons to remove bone. Such systems often generate bone fragments (in many instances with a drill). Once removed, the bone fragments, collectively referred to as bone graft, can be reused. In fact, the bone graft is particularly useful in various surgical procedures because it can be used to bridge gaps between bone segments and provide a natural foundation for bone growth.

In some surgical procedures, the bone fragments are, as a matter of course, necessarily generated, harvested, and used as bone graft all in the same procedure. For example, spinal procedures (e.g. discectomy) require the drilling and removal of various spinal bone, and the subsequent use of bone graft. As another example, joint reconstruction and revision procedures require the drilling and removal of various bone, and the subsequent use of bone graft.

In other surgical procedures, the bone fragments may be intentionally harvested, sometimes from bones in another area of the body, for use in the procedure that requires bone graft. In yet other procedures, bone graft comprising bone from another patient, a cadaver, pig, or even synthetic bone material can be used. Bone graft comprising natural bone, especially bone harvested from a patient for use on the same patient (sometimes referred to as autograft) is preferred by surgeons because of its osteoconductive, osteoinductive, and osteogenic properties.

While bone collection and processing systems have generally performed well for their intended use, there remains the need to maximize bone fragment recovery and process the bone fragments in a sterile and efficient manner.

BRIEF DESCRIPTION OF THE DRAWINGS

Advantages of the examples disclosed herein will be readily appreciated as the same becomes better understood after reading the subsequent description taken in connection with the accompanying drawings.

FIG. 3 is a partially exploded side view of the device of FIG. 1, shown with the chamber member decoupled from the press member with a portion of the chamber member shown transparent such that threads on an inner peripheral surface of a chamber side wall of the chamber member, which cooperate with threads on an outer peripheral surface of a press side wall to rotationally couple the chamber member and the press member, are visible.

FIG. 4 is a partially exploded side view of the device of FIG. 1, shown with a compression surface support structure of the chamber member isolated with a compliant member which comprises a compliant material thereon defining the compression surface.

FIG. 14 is a cross-sectional view of the device of FIG. 10 taken along B-B and applied to the side view of the device shown in FIG. 13.

DETAILED DESCRIPTION

Figure 1:
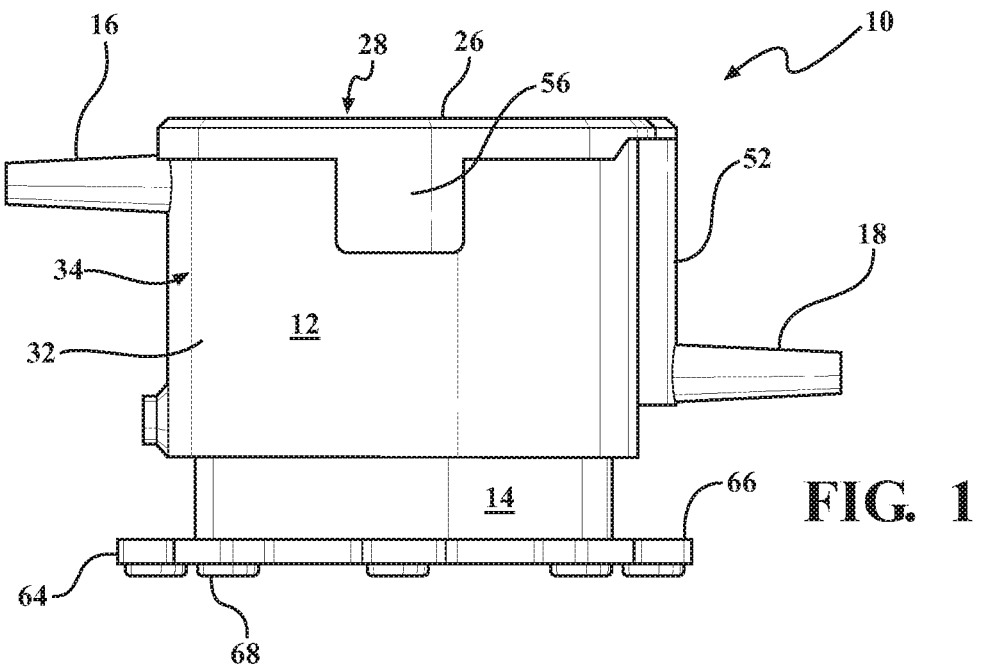
FIG. 1 is a side view of a device for collecting and processing bone fragments according to one example, shown with a chamber member and a press member rotationally coupled with one another.

With reference to the drawings, where like numerals are used to designate like structures throughout the several views, a device for collecting and processing bone fragments ("the device") is shown at 10 in FIG. 1. The device 10 of the subject disclosure is configured to collect and process bone fragments in connection with various types of medical and/or surgical procedures. More specifically, the device 10 is configured to process and collect a composition comprising bone fragments $C_{BF}$, and other components ("the composition $C_{BF}$") from a patient. The term bone fragments, as used herein, is intended to be broadly construed to encompass all bone components regardless of their form, e.g. bone, tissues such as stem and progenitor cells, etc. Once processed, the composition $C_{BF}$ is typically used to form bone graft.

Figure 21:
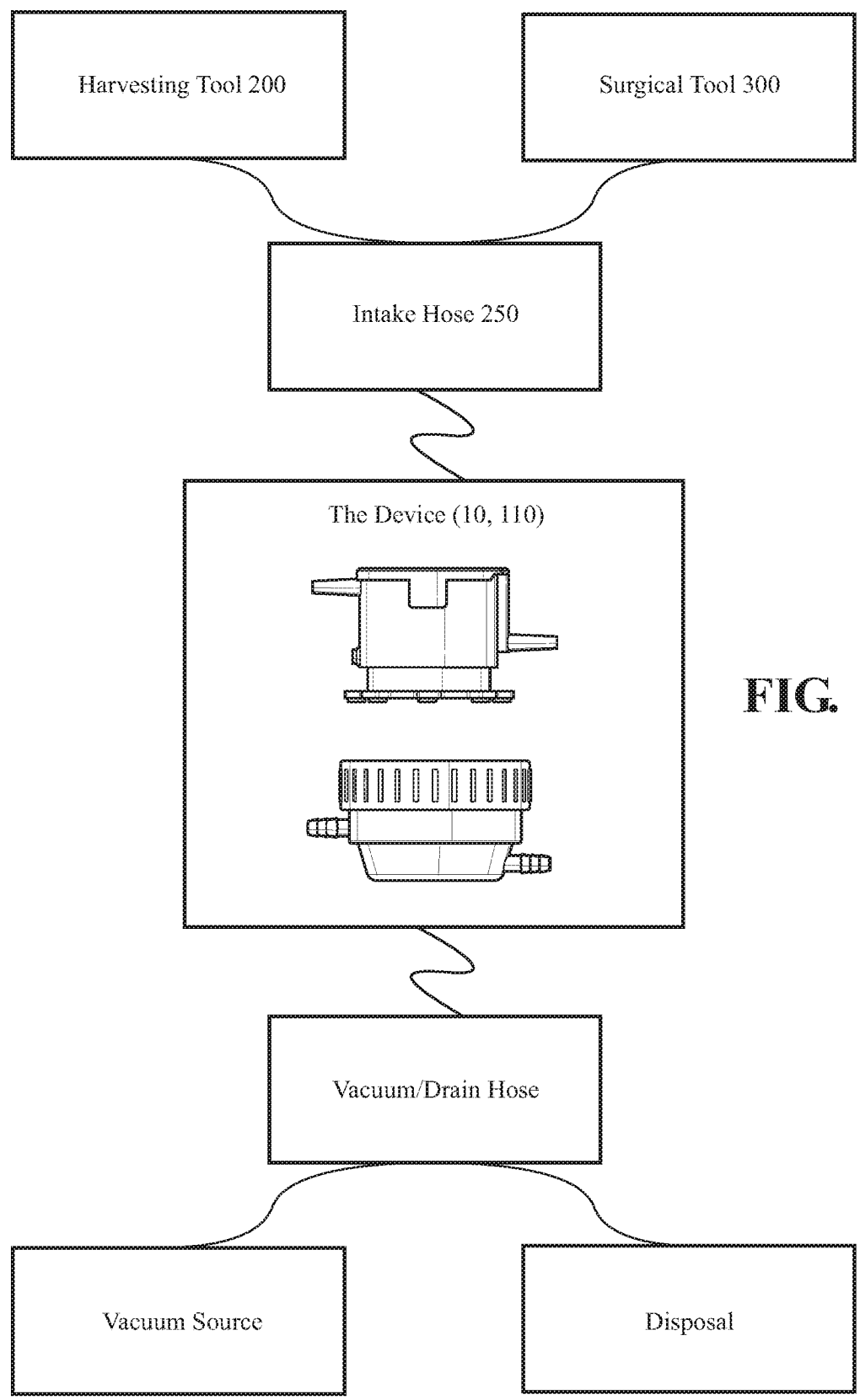
FIG. 21 is a flow diagram describing a system including the device.

In additional aspects, the subject disclosure further provides a system, generally described in FIG. 21, for use in collecting and processing composition $C_{BF}$. The system includes a harvesting tool 200 configured to harvest the composition $C_{BF}$ and shaped to couple with an intake hose 250. In some examples, the system also comprises a surgical tool 300 configured to generate, e.g. grind, cut, shave, or abrade, bone to yield bone fragments. In some examples, the system includes the surgical tool 300 configured to both generate bone fragments and harvest, i.e., aspirate, the composition $C_{BF}$. The system also includes the intake hose 250 through which the composition $C_{BF}$ is conveyed from the harvesting tool 200 (or the surgical tool 300) to the device 10 for collecting and processing bone fragments. In a typical example, the composition $C_{BF}$ is aspirated from the patient using the harvesting tool 200, which causes the aspirated composition $C_{BF}$ to be collected in the device 10.

Figure 2:
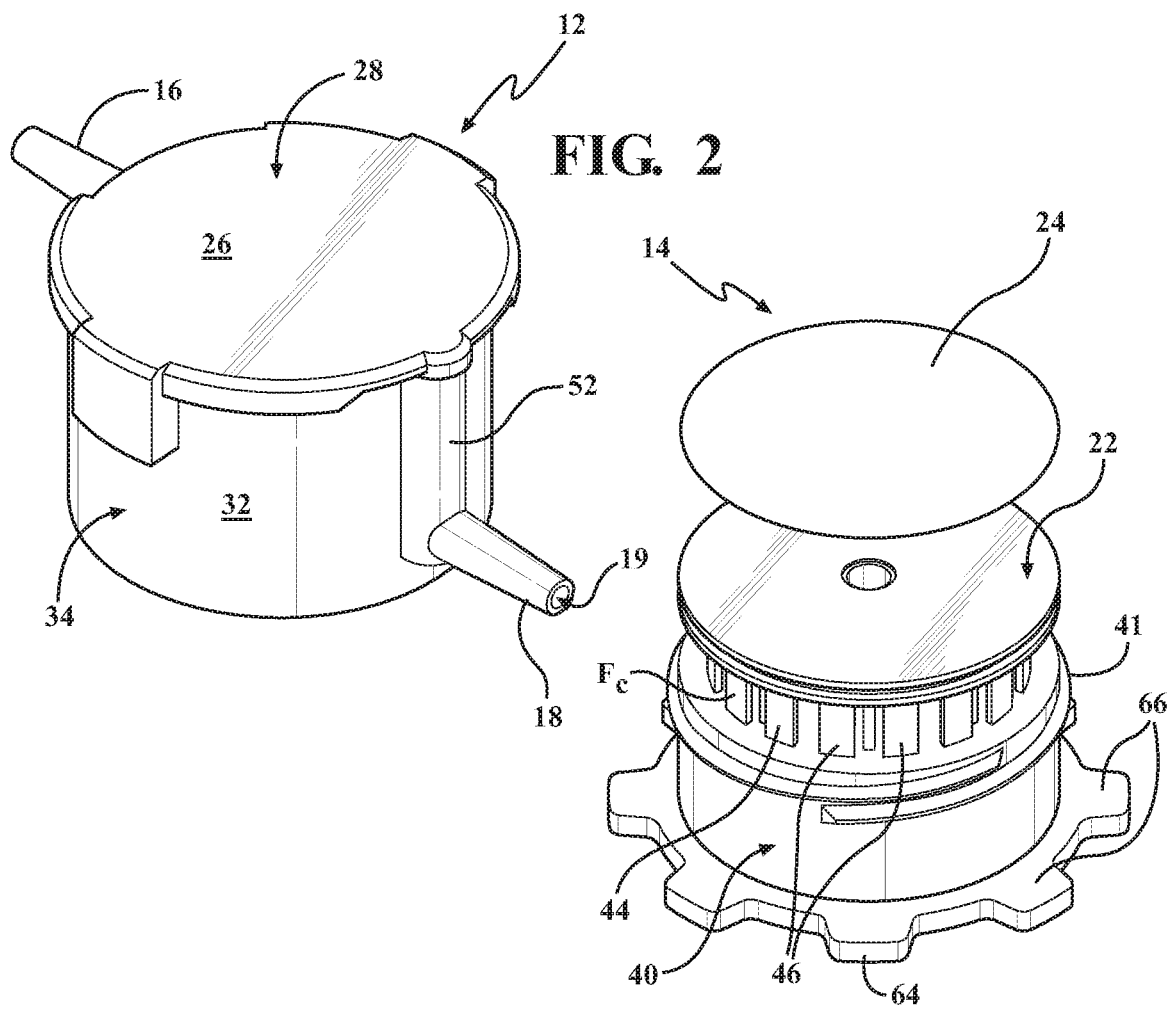
FIG. 2 is a perspective view of the device of FIG. 1, shown with the chamber member decoupled from the press member.

As an overview, a representative example of the device 10 is illustrated throughout the FIGS. 1-17A-D and includes a chamber member 12, a press member 14, an intake port 16, and a vacuum port 18 (e.g. FIGS. 1 and 2). A filter support surface 22 (shown in FIGS. 2 and 3) is configured to support a filter 24 and cooperate with a compression surface 20 (shown in FIG. 3). Although the filter support surface 22 (shown in FIGS. 2 and 3) is configured to support a filter 24, it typically includes apertures or the like which allow the flow fluid through the filter and out of the device 10. The filter support surface 22 and the compression surface 20 are defined by the chamber and/or press member 12, 14. For example, in FIGS. 1-9 the filter support surface 22 is defined by the press member 14, and in FIGS. 10-17A-D the filter support surface 122 is defined by a chamber member 112. For example, in FIGS. 1-9 the compression surface 20 is defined by the chamber member 12, and in FIGS. 10-17A-D the compression surface 120 is defined by the chamber member 112. The intake port 16 is on the chamber member 12, but can also be located on the press member 14. The intake port 16 is configured to receive composition $C_{BF}$. The vacuum port 18 is shown on the chamber member 12 and is configured to be coupled to a vacuum. The vacuum port 18 may also be included as part of the press member 14.

Figure 9:
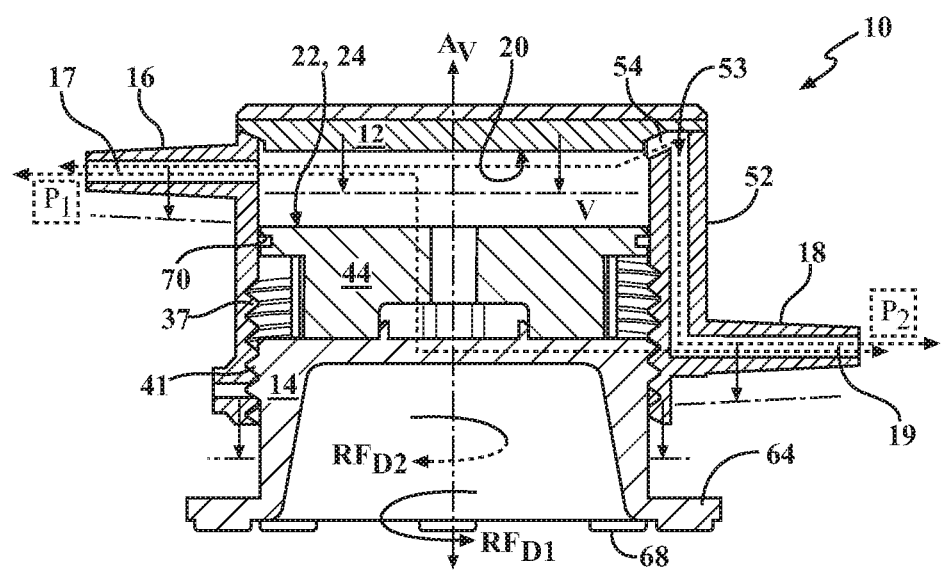
FIG. 9 is a schematic illustration of a cross-sectional view of the device of FIG. 5 taken along A-A which further illustrates the application of rotational force to the chamber member in a first direction and the subsequent movement of the compression surface and the filter support surface (depicted in phantom with dashed lines) together and the compression of the composition therebetween to compact, and further remove filtrate (liquid) components from the composition.

The chamber member 12 and the press member 14 are rotationally coupled with one another to cause relative axial movement between one another. The composition $C_{BF}$ is acquired through the intake port 16 and collected in the volume V between the compression surface 20 and the filter support surface 22, more specially between the compression surface 20 and the filter support surface 22. Referring now to FIG. 9, the application of rotational force to the press member 14 in a first direction $RF_{D1}$ moves the compression surface 20 and the filter support surface 22 together to compress the composition $C_{BF}$ therebetween to compact, and further remove filtrate (liquid) components from the composition $C_{BF}$. It should be appreciated that the application of rotational force to the chamber member 12 in a direction opposite the first direction described immediately above also moves the compression surface 20 and the filter support surface 22 together to compress the composition $C_{BF}$ therebetween to compact, and further remove filtrate (liquid) components from the composition $C_{BF}$.

As discussed herein, reference to the application of rotational force in a first direction generally refers to a tightening motion which moves the compression surface 20 and the filter support surface 22 closer to one another, and the application of rotational force in a second direction, opposite the first direction, generally refers to a loosening motion which moves the compression surface 20 and the filter support surface 22 away from one another, and in some examples, may even disengage the members 12, 14. To this end, when these directional terms are used, it is to be appreciated that these directions apply application of force to a specific member in a specific orientation.

Referring now to FIG. 1, a side view of a first example of the device 10 is illustrated with the chamber member shown at 12 and the press member shown at 14. In the example of FIG. 1, which is illustrated throughout FIGS. 1-9, the chamber member 12 includes the intake port 16 and the vacuum port 18.

FIG. 2 is a perspective view of the chamber member 12 decoupled from the press member 14. As is shown in FIGS. 2-9, the chamber member 12 and the press member 14 may be rotationally coupled with one another. As such, in certain configurations, the chamber member 12 may cylindrical and has a chamber end 26 and a chamber side wall 32 which together at least partially define the volume V. The chamber end 26 has an outer surface 28 and an inner surface 30. In some examples, the chamber end 26 is removably attached to the chamber side wall 32, to function as a lid and allow access to the composition $C_{BF}$ without decoupling the chamber member 12 and the press member 14. In certain examples, the chamber top may be fixed to the chamber side wall 32. The chamber side wall 32 has an outer peripheral surface 34 and an inner peripheral surface 36.

FIG. 3 is a partially exploded side view of the device 10, shown with the chamber member 12 decoupled from the press member 14 and with the chamber end 26 decoupled from the chamber sidewall 32. In FIG. 3, the chamber end 26 is operably attached to the chamber side wall 32 with a coupling mechanism. The coupling mechanism may take various forms, but in the illustrated example, the coupling mechanism comprises tabs 56 which are located on an outer circumference of the chamber end 26 and each tab has an inner surface (not shown) defining an engagement channel; and (2) engagement projections (not shown) on the outer peripheral surface 34 of the chamber side wall 32 which are shaped to engage the engagement channel.

As illustrated, the chamber side wall 32 extends longitudinally from the chamber end 26 along the vertical axis Av and has the outer peripheral surface 34 and an inner peripheral surface 36. In some examples, the chamber end 26 and/or the chamber side wall 32 are substantially transparent so that the composition $C_{BF}$ collected between the compression surface 20 and the filter support surface 22 can be visually monitored by a user of the device 10.

The chamber member 12 and the press member 14 function like a piston/cylinder arrangement and compress the composition $C_{BF}$ between the compression surface 20 and the filter support surface 22 as is described in greater detail below. Further, in a typical example, the compression surface 20 and the filter support surface 22 are substantially parallel. As disclosed above, the chamber member 12 defines the compression surface 20. In some examples, the inner surface 30 of the chamber end 26 of the chamber member 12 defines the compression surface 20. In other examples, the chamber member 12 includes a compression surface support structure 48 which is operably attached to the inner peripheral surface 36 of the chamber side wall 32 of the chamber member 12 and supports a compliant member 50.

FIG. 4 is a partially exploded side view of the device 10, shown with the compression surface support structure 48 of the chamber member 12 isolated with the compliant member 50 thereon defining the compression surface 20. That is, in some examples, the chamber member 12 further includes the compliant member 50 which defines the compression surface 20.

The compliant member 50 comprises, consists essentially of, or consists of, a compliant material, typically a polymer, and allows for the consistent application of force to the composition $C_{BF}$ such that the bone fragments, often having an irregular shape, do not cause a reduction in compression force when rotational force is applied to the chamber and/or press member 12, 14 in a first direction $RF_{D1}$ to move the compression surface 20 and the filter support surface 22 together with the composition $C_{BF}$ therebetween. As such, the composition $C_{BF}$ is compressed and filtered to provide a homogenous product of consistent quality.

The compliant member 50 typically comprises, consists essentially of, or consists of, a compliant material, typically a polymer, and allows for the consistent application of force to the composition $C_{BF}$ such that the bone fragments, often having an irregular shape, do not cause a reduction in compression force when rotational force is applied to the chamber and/or press member 12, 14 in a first direction $RF_{D1}$ to move the compression surface 20 and the filter support surface 22 together with the composition $C_{BF}$ therebetween.

The compliant material typically comprises one or more polymers. In some examples, the compliant material is selected from elastomers, thermoplastics, thermoplastic elastomers, and combinations thereof.

Various non-limiting examples of suitable elastomers include natural rubber (natural polyisoprene), synthetic polyisoprene, polybutadiene, chloroprene rubber, butyl rubber, halogenated butyl rubber, styrene-butadiene rubber, nitrile rubber, ethylene propylene rubber, ethylene propylene diene rubber, epichlorohydrin rubber, polyacrylic rubber, silicone rubber, fluorosilicone rubber, fluoroelastomer, perfluoroelastomer, polyether block amides, chlorosulfonated polyethylene, and ethylene-vinyl acetate. In a preferred example, the compliant material comprises silicone.

Various non-limiting examples of suitable thermoplastics and thermoplastic elastomers include polyolefins, polyolefin elastomers, polyvinylchlorides (PVC), polyamides (PA), styrenic elastomers, thermoplastic vulcanate elastomer (TPV), fluoropolymers, silicones, polyesters, polyoxymethylenes (POM), thermoplastic polyurethanes (TPU), and combinations thereof. In some preferred examples, the polymer is selected from thermoplastic polyurethane, polyoxymethylene, polyalkylene terephthalate, and combinations thereof.

In some examples, the compliant material comprises polymer, such as, but not limited to, those immediately described above, which has a Shore A hardness of from about 30 to about 60, or from about 35 to about 50, when tested in accordance with ASTM D2240, Standard Test Method for Rubber Property—Durometer Hardness. In various non-limiting examples, all values and ranges of values between the aforementioned values are hereby expressly contemplated.

The complaint properties of the compliant material, such as the Shore A hardness properties defined above, ensure that consistent, even force is applied to the composition $C_{BF}$ which is compressed and filtered to provide a homogenous product of consistent quality.

In examples not specifically shown in the Figures but contemplated herein, the compliant member 50 comprises the compliant material and includes a cavity, which can be deflated when rotational force is applied to the chamber and/or press member 12, 14 in a first direction $RF_{D1}$ to move the compression surface 20 and the filter support surface 22 together with the composition $C_{BF}$ therebetween. As such, consistent, even force is applied to the composition $C_{BF}$ which is compressed and filtered to provide a homogenous product of consistent quality.

Figure 10:
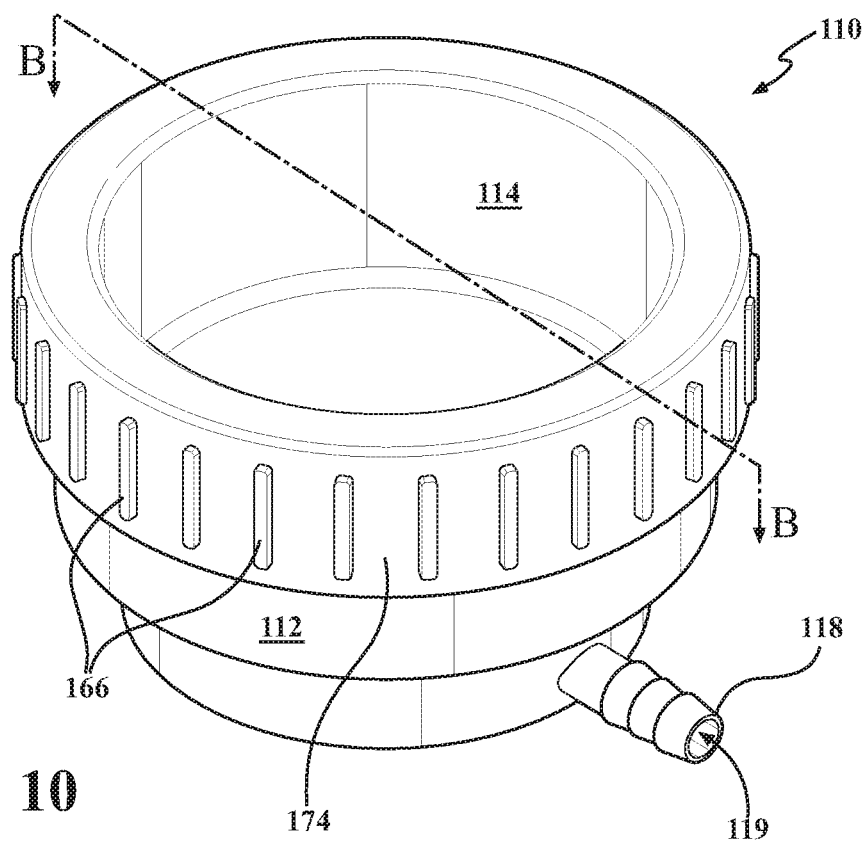
FIG. 10 is a perspective view of another example of the device for collecting and processing bone fragments with the chamber member and the press member shown rotationally coupled with one another.

Referring to FIG. 1 or FIG. 10, in a typical example, the press member 14 is cylindrical; however, still other shapes are contemplated. The press member 14 may include a press side wall 38 having an outer peripheral surface 40 and an inner peripheral surface 42. In a typical example, the press member 14 further defines the volume V and comprises a filter support structure 44 which at least partially defines a filtrate collection chamber Fc within the volume V. In the examples shown throughout the Figures, the filter support structure 44 comprises a plurality of support columns 46 and is configured to support the filter 24 and allow for the collection and removal of liquid (filtrate) which passes through the filter 24. An isolated view of the filter support structure 44 is shown the FIG. 7. In other words, the filter support structure 44 is permeable to allow suction therethrough. It is arranged to support the filter 24. In various examples, the filter support structure 44 includes contact points in the form of columns, a circumferential rim of the inner peripheral surface of the respective member, etc., which constitute a contact point upon which the filter 24 can be secured. In some examples, a locking mechanism (not shown) is used to secure the filter 24 in the filter support structure 44.

In examples not specifically shown in the Figures but contemplated herein, the filter support surface 22 is further defined by a filter cartridge. In such examples, the filter cartridge can be removably and/or operatively attached to the chamber member 12 and/or the press member 14. The filter cartridge is removably attached to the device 10. The filter cartridge can be disposable or reusable (e.g. can be cleaned via autoclave and reused). As a non-limiting example, the filter cartridge which defines the filter support surface 22 and includes the filter 24, can be attached in a channel or on a ridge formed on the inner peripheral surface 36 of the chamber side wall 32 or the inner peripheral surface 42 of the of the press side wall 38. In one example, the device 10 can be used, and the filter cartridge subsequently disposed of. The device 10 can then be cleaned, e.g. autoclaved, and a new, unused cartridge can be attached to the device 10 which can then be used again. To this end, a method further comprises the step of inserting and/or removing the filter cartridge from the volume V.

Figure 5:
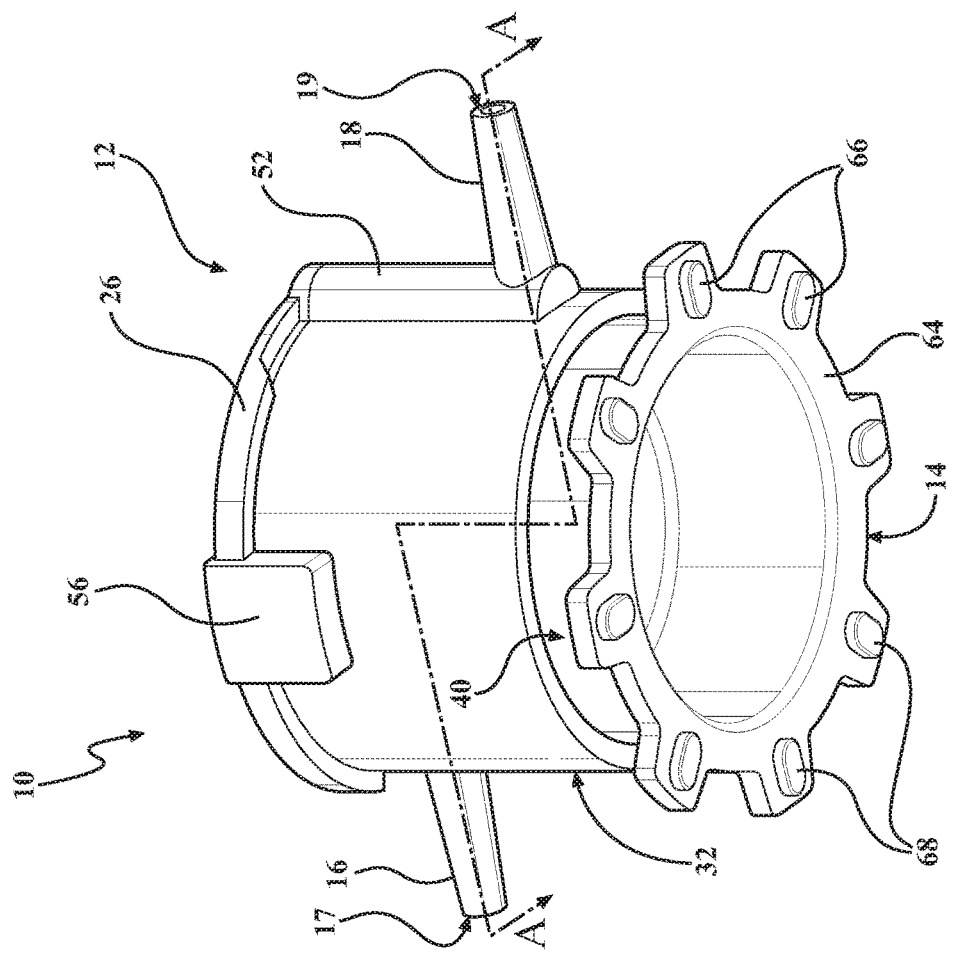
FIG. 5 is a bottom perspective view of the device of FIG. 1 showing the foundational element including grip tabs.

The inner peripheral surface 36 of the chamber side wall 32 of the chamber member 12 is shaped to rotatably engage the outer peripheral surface 40 of the press side wall 38 of the press member 14. In a preferred example, the inner peripheral surface 36 of the chamber side wall 32 and the outer peripheral surface 40 of the press side wall 38 are threaded (or are in threaded engagement). The threaded sidewall of the example of FIGS. 1-9 are shown throughout the various views of FIGS. 2-9. In FIGS. 3, 4, and 5, the sidewall 32 of the chamber member 12 is shown transparent such that threads 37 on the inner peripheral surface 36 of the chamber side wall 32 of the chamber member 12 and threads 41 on the outer peripheral surface 40 of the press side wall 38, which cooperate to rotationally couple the chamber member 12 and the press member 14, are visible.

Figure 8:
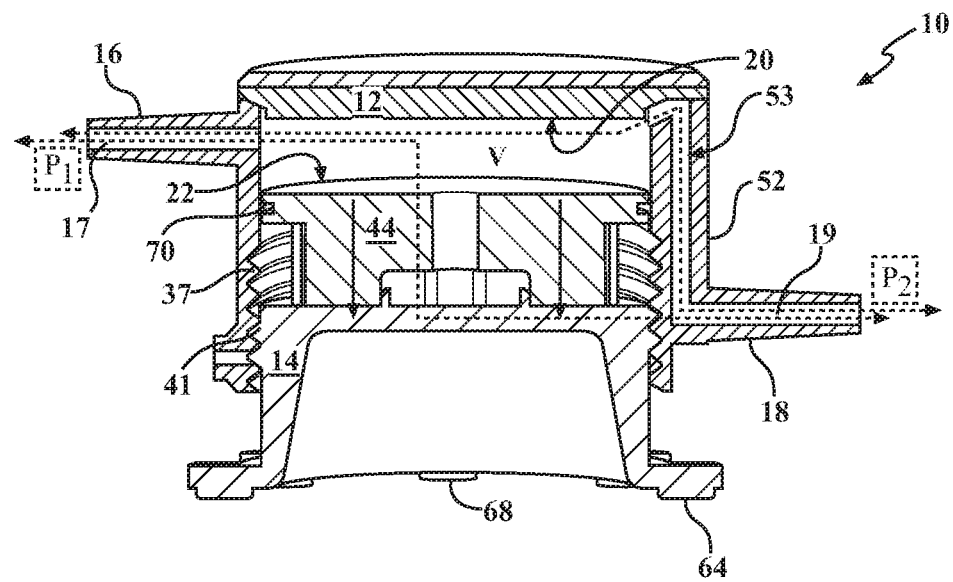
FIG. 8 is a schematic illustration of a cross-sectional view of the device of FIG. 5 taken along A-A which illustrates a fluid communication path wherein a composition is drawn into the device through an input port and into a volume between the compression surface and a filter support surface having a filter thereon, and filtrate is drawn through a filter and out of a vacuum port.

Various examples of the device 10 include at least one intake port 16 which can be alternatively referred to as an input fitting 16. As is shown in FIGS. 8 and 9, the intake port 16 defines a bore 17 and is in fluid communication with the volume V, with the intake port 16 adapted to receive the intake hose 250 for drawing the composition $C_{BF}$ into the volume V. A fluid communication path $P_1$ is established from an intake bore 17 of the intake port 16 through the volume V and across the filter support surface 22 having the filter 24 thereon through to the vacuum port 18 which defines a vacuum bore 19 and can be alternatively referred to as an output fitting 18. FIG. 8 is a schematic illustration of a cross-sectional view of the device 10 which further illustrates the intake of composition $C_{BF}$ into the device 10 through the intake port 16 and into the volume V between the compression surface 20 and the filter support surface 22 having the filter 24 thereon, and the removal of filtrate drawn through the filter 24 and out of the vacuum port 18. To this end, the device 10 functions via vacuum or aspiration across the fluid communication path $P_1$.

As is illustrated in FIGS. 8 and 9, the composition $C_{BF}$ is drawn into the device 10 through the intake port 16 and into the volume V between the compression surface 20 and the filter support surface 22 having the filter 24 thereon. The composition $C_{BF}$ collects in the volume V between the compression surface 20 and the filter support surface 22 while fluid is drawn through the fluid communication path $P_1$. As the composition $C_{BF}$ is drawn through the fluid communication path $P_1$, the composition $C_{BF}$ collects within the volume V on the filter 24 and excess fluid is drawn out of the vacuum port 18.

Figure 6:
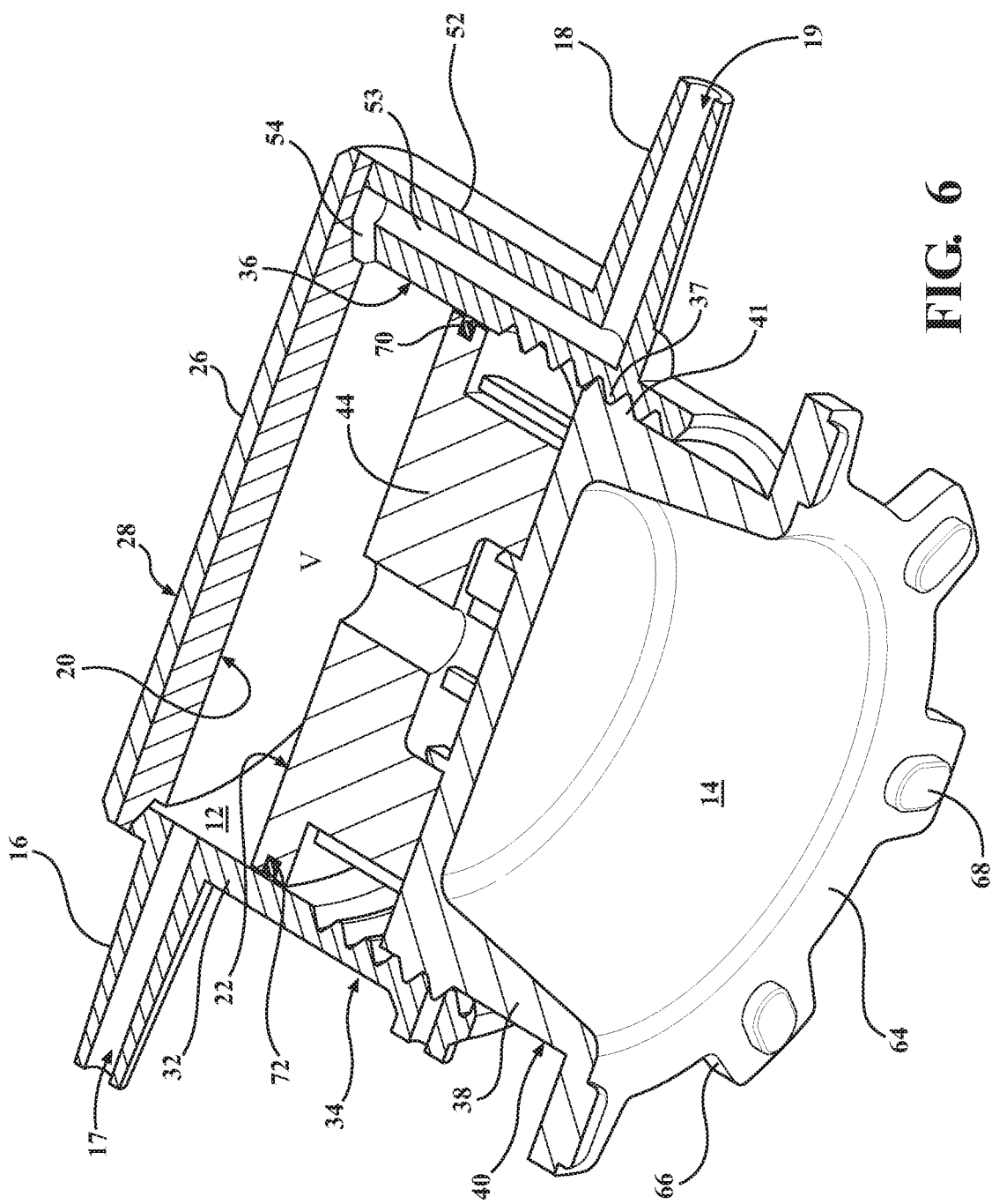
FIG. 6 is a sectional view taken along A-A of FIG. 5.

FIG. 5 is a bottom perspective view of the device 10 and FIG. 6 is a cross-sectional view taken along A-A of FIG. 5 showing the fluid communication path $P_1$ through which the composition $C_{BF}$ is drawn into the device 10 through the intake port 16 and into the volume V between the compression surface 20 and the filter support surface 22 having the filter 24 thereon, and filtrate is drawn through the filter 24 and out of the vacuum port 18.

Figure 7:
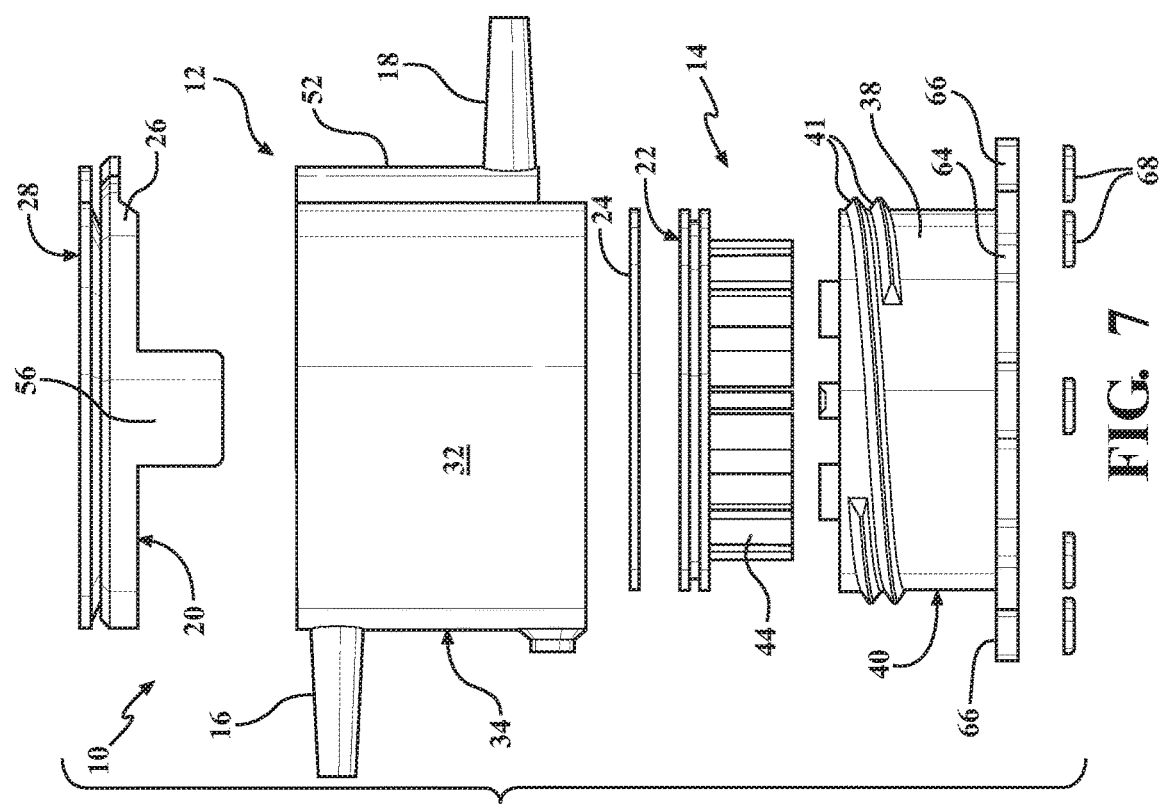
FIG. 7 is an exploded side view of the device of FIG. 5 isolating the chamber end, a filter surface support structure, and the grip pads of the stabilizer tabs of the foundational element.

Further, FIG. 5 also shows an optional foundational element 64 including one or more grip tabs 66 and one or more pads 68. The foundational element 64 stabilizes the device 10 during use in an upright position on a surface. Referring now to FIG. 6, the press side wall 38 of this example defines a groove 70 for an o-ring 72. FIG. 7 is an exploded side view of the device 10 which isolates the pads 68 of the grip tabs 66 of the foundational element 64.

Referring back to FIGS. 6, 8, and 9, in some examples, the device 10 comprises a snorkel 52. In certain examples, the snorkel 52 is a generally tubular structure. In the example of FIGS. 1-9, the snorkel 52 defines a bore 53 and has a suction port 54 above the compression surface 20 and is in fluid communication with the vacuum port 18 and the volume V. The snorkel 52 is configured to remove filtrate from the composition $C_{BF}$ between the compression surface 20 and the filter support surface 22 via an alternative fluid communication path $P_2$. As an amount of the composition $C_{BF}$ begins to accumulate between the compression surface 20 and the filter support surface 22, the snorkel 52 provides the second fluid communication path $P_2$. For example, the composition $C_{BF}$ begins to accumulate between the compression surface 20 and the filter support surface 22 such that the filter 24 clogs to block fluid communication patch P1, the snorkel 52 provides the second fluid communication path $P_2$ to prevent clogging. Referring now to FIGS. 1-9, the snorkel 52 is shown as an integral component of the chamber member 12. However, it should be appreciated that the snorkel 52 may be a distinct component. FIGS. 8 and 9 show the snorkel 52 is positioned on the chamber side wall 32, and substantially perpendicular to the compression surface 20 and the filter support surface 22 and perpendicular to the vertical axis $A_v$. However, other snorkel arrangements are contemplated.

As is shown in FIGS. 2-4, the filter 24 is typically utilized in the device 10. The filter 24 can be fixed, or the filter 24 can be disposable. The filter 24 can comprise metal or polymer. In one example, the filter 24 comprises stainless steel. In many examples, the filter 24 has a U.S. Sieve Series mesh size of from about 12 to about 500 (from about 1.68 to about 0.025 mm), or from about 50 to about 270 (from about 0.297 to about 0.053 mm).

As set forth above, the inner peripheral surface 36 of the chamber side wall 32 of the chamber member 12 is shaped to rotatably engage the outer peripheral surface 40 of the press side wall 38 of the press member 14, e.g. the inner peripheral surface 36 of the chamber side wall 32 and the outer peripheral surface 40 of the press side wall 38 are threaded (or are in threaded engagement). As illustrated in FIGS. 8 and 9, the composition $C_{BF}$ is acquired through the intake port 16 and collected between the compression surface 20 and the filter support surface 22 with the filter 24 thereon. Once the composition $C_{BF}$ is collected between the compression surface 20 and the filter support surface 22, the application of rotational force to the press member 14 in the first direction RFD' moves the compression surface 20 and the filter support surface 22 together to compress the composition $C_{BF}$ therebetween to further filter and compact the composition $C_{BF}$. FIG. 9 is a schematic illustration which further illustrates the application of rotational force to the chamber member 12 in the first direction RFD' and the subsequent movement of the compression surface 20 and the filter support surface 22 (with movement illustrated with arrows and in phantom with dashed lines) together and the compression of the composition $C_{BF}$ therebetween to compact, and further remove filtrate (liquid) components from the composition $C_{BF}$.

Further, the application of rotational force to the chamber member and/or press member 12, 14 in a second direction $RF_{D2}$, opposite the first direction RFD', moves the compression surface 20 and the filter support surface 22 away from one another. In some examples, the application of rotational force to the chamber and/or press member 12, 14 in the second direction $RF_{D2}$ allows for decoupling of the chamber member 12 and the press member 14, and access to the compacted composition $C_{BF}$ for removal. FIG. 2 shows the chamber member 12 decoupled from the press member 14, with the threads 41 on the outer peripheral surface 40 of the press side wall 38 visible. In other examples, the chamber end 26 is operably attached to the chamber side wall 32, to function as a lid and allow access to the filtered and compacted composition $C_{BF}$ for removal.

As set forth above, the intake port 16 is configured to receive the composition $C_{BF}$ comprising bone fragments and the vacuum port 18 is shown on the chamber 12 and is configured to be coupled to a vacuum. Typically, the ports 16, 18 will both be located on the same member 12, 14 to facilitate ease of use. In the examples shown in the Figures, the intake port 16 and the vacuum port 18 are both located on the chamber side wall 32 of the chamber member 12 about 180° from one another. The location of the intake and vacuum ports 16, 18 is believed to (1) minimize vacuum loss and (2) aid in work flow during operation of the device 10 (e.g. facilitate the process of fitting of the intake hose 250 on the intake port 16 and a vacuum and/or fluid removal line on the vacuum port 18). In FIGS. 1-9, the intake port 16 and the vacuum port 18 are both on the chamber member 12. In FIGS. 10-17A-D, the intake port 116 and the vacuum port 118 are both on the chamber member 112. When both ports 16, 18 are on the same member, the intake hose 250 and the vacuum/drain hose will not get tangled during use because a user will naturally twist (apply force) to the respective member 12, 14 without the hoses attached thereto. Further, the outer peripheral surface of the member (of either member 12, 14) without the ports 16, 18 can be configured to have a grip for the user on the outer peripheral surface of its side wall 34, 40. For example, the foundational element 64 on the chamber member 12 of FIGS. 1-9, includes grip tabs 66 which can be used to twist the chamber member 12. That is, the grip tabs 66 provide a user with good grip to facilitate easy use of the device 10. As another example, an outer peripheral surface 140 of a press sidewall 138 of the press member 114 of FIGS. 10-17A-D includes grip ridges 166 which can be used to twist the press member 114. The grip ridges 166 provide the user with good grip to facilitate easy use of the device 110.

Referring now to FIGS. 10-17A-D, a second example of the device 110 for collecting and processing bone fragments is illustrated. The device 110 of this example includes the chamber member 112, the press member 114, the intake port 116, and the vacuum port 118. In this example, the chamber member 112 defines the filter support surface 122 which is configured to support the filter 124 and at least partially defines the volume V. Further, the chamber member 112 includes the intake port 116 which is configured to receive the composition $C_{BF}$ and the vacuum port 118 which is configured to be coupled to a vacuum source. In this example, the press member 114 defines the compression surface 120.

To this end, the example of FIGS. 10-17A-D includes the chamber member 112 defining the filter support surface 122, and the press member 114 defining the compression surface 120, whereas the example of FIGS. 1-9 includes the chamber member 12 defining the compression surface 20 and the press member 14 defining the filter support surface 22. Further, in the example of FIGS. 10-17A-D, the device 110 is shown sitting upright with the chamber member 112 resting on a surface and the press member 114 above the chamber member 112, whereas in the example of FIGS. 1-9, the device 10 is depicted in an upright position with the press member 14 resting on a surface and the chamber member 12 above the press member 14.

The chamber member 112 and the press member 114 are rotationally coupled with one another. The composition $C_{BF}$ is acquired through the intake port 116 and collected between the compression surface 120 and the filter support surface 122. The application of rotational force to the chamber and/or press member 112, 114 in a first direction $RF_1$ moves the compression surface 120 and the filter support surface 122 together to compress the composition $C_{BF}$ therebetween to compact, and further remove filtrate (liquid) components from the composition $C_{BF}$.

Figure 11:
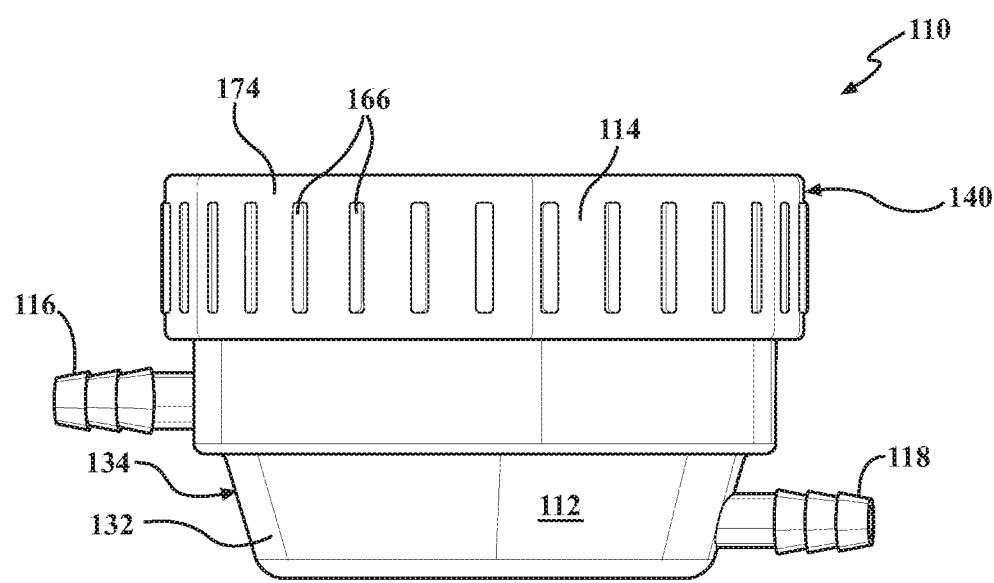
FIG. 11 is a side view of the device of FIG. 10 which shows the chamber member including the intake port and the vacuum port located on the chamber side wall of the chamber member spaced from one another.

FIG. 10 is a perspective view of another example of the device 110 with the chamber member 112 and the press member 114 shown rotationally coupled with one another. FIG. 11 is a side view of the device 110 of FIG. 10 which shows the chamber member 112 including the intake port 116 and the vacuum port 118 located on the chamber side wall 132 of the chamber member 112 about 180° from one another.

Figure 12:
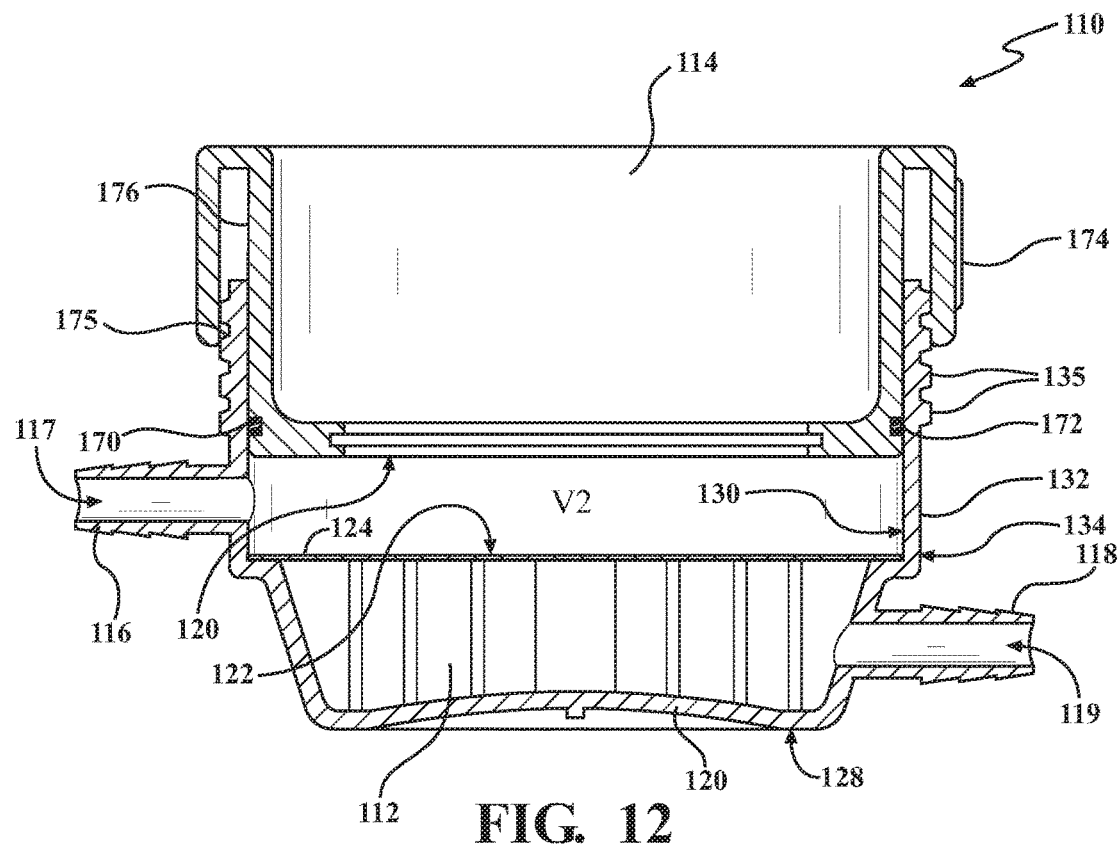
FIG. 12 is a cross-sectional view of the device of FIG. 10 taken along B-B and applied to the side view of the device as shown in FIG. 11.

FIG. 12 is a cross-sectional view of the device 110 of FIG. 10 taken along B-B of FIG. 10 and applied to the side view of the device 110 as shown in FIG. 11. FIG. 12 illustrates the fluid communication path $P_1$. When the device 110 is in use, the composition $C_{BF}$ is drawn into the device 110 through the intake port 116 and into the volume V2 between the compression surface 120 and the filter support surface 122 having a filter 124 thereon. The composition $C_{BF}$ collects in the volume V between the compression surface 120 and the filter support surface 122 while fluid is drawn through the fluid communication path $P_1$. As the composition $C_{BF}$ is drawn through the fluid communication path $P_1$, the composition $C_{BF}$ collects within the volume V on the filter 124 and excess fluid is drawn out of the vacuum port 118.

Figure 13:
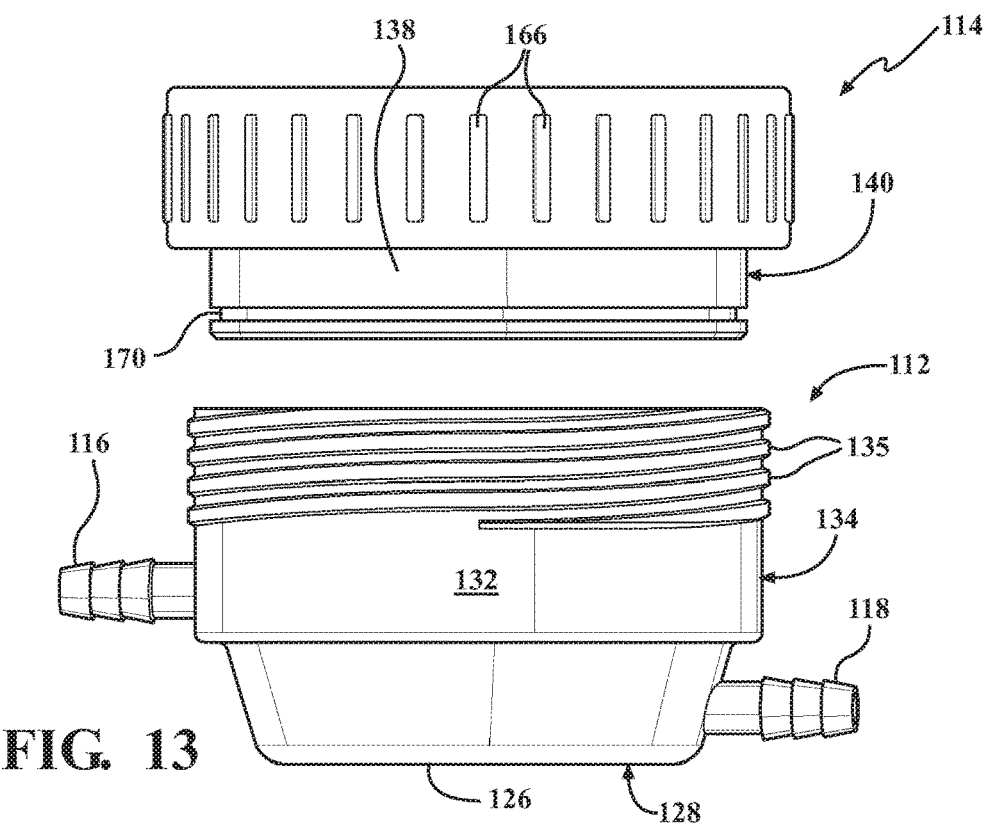
FIG. 13 is a side view of the device of FIG. 10 with the chamber member decoupled from the press member.

In this example, the chamber member 112 is cylindrical and has the chamber end 126 and chamber side walls 132 which together define the volume V2. Typically, as shown, the chamber member 112 is cylindrical. The chamber end 126 has an outer surface 128 and an inner surface 130. The chamber side wall 132 has an outer peripheral surface 134 and an inner peripheral surface 136. FIG. 14, which is a cross-sectional view of the device 110 of FIGS. 10-17A-D taken along B-B of FIG. 10 and applied to the side view of the device 110 shown in FIG. 13, shows the filter support surface 122 and a filter support structure 144 disposed in the volume V. The filter support structure 144 defines the filter support surface 122 and the filtrate collection chamber Fc within the volume V. In this example, the filter support structure 144 comprises a plurality of support columns 146 and is configured to support the filter 124 and allow for the collection and removal of liquid (filtrate) which passes through the filter 124. Of course, various other support structure 144 configurations are contemplated.

In this example, the press member 114 is cylindrical and has the press side wall 138 having the outer peripheral surface 140 and an inner peripheral surface 142. Referring now to FIG. 12, the press side wall 138 of this example defines a groove 170 for an o-ring 172 and includes an engagement sleeve 174 having a threaded inner surface 176 and shaped to engage and operatively couple with the chamber side wall 132 of the chamber member 112, which is threaded.

Still referring to FIG. 12, the outer peripheral surface 134 of the chamber side wall 132 of the chamber member 112 is shaped to rotatably engage the outer peripheral surface 140 of the press side wall 138 of the press member 114. In this example, the outer peripheral surface 134 of the chamber side wall 132 includes threads 135, and the engagement sleeve 174 of the press member 114 has an inner surface 176 which includes threads 175 and are thus shaped to rotatably engage one another.

FIG. 13 is a side view of the chamber member 112 decoupled from the press member 114. FIG. 14, which is a cross-sectional view of the device 110 of FIG. 12 taken along B-B, shows the threading 175 on the inner surface 176 of the engagement sleeve 174 of the press member 114 which cooperates with the threading 135 on the outer peripheral surface 134 of the chamber side wall 132 to rotationally couple the press member 114 and the chamber member 112.

Figure 15:
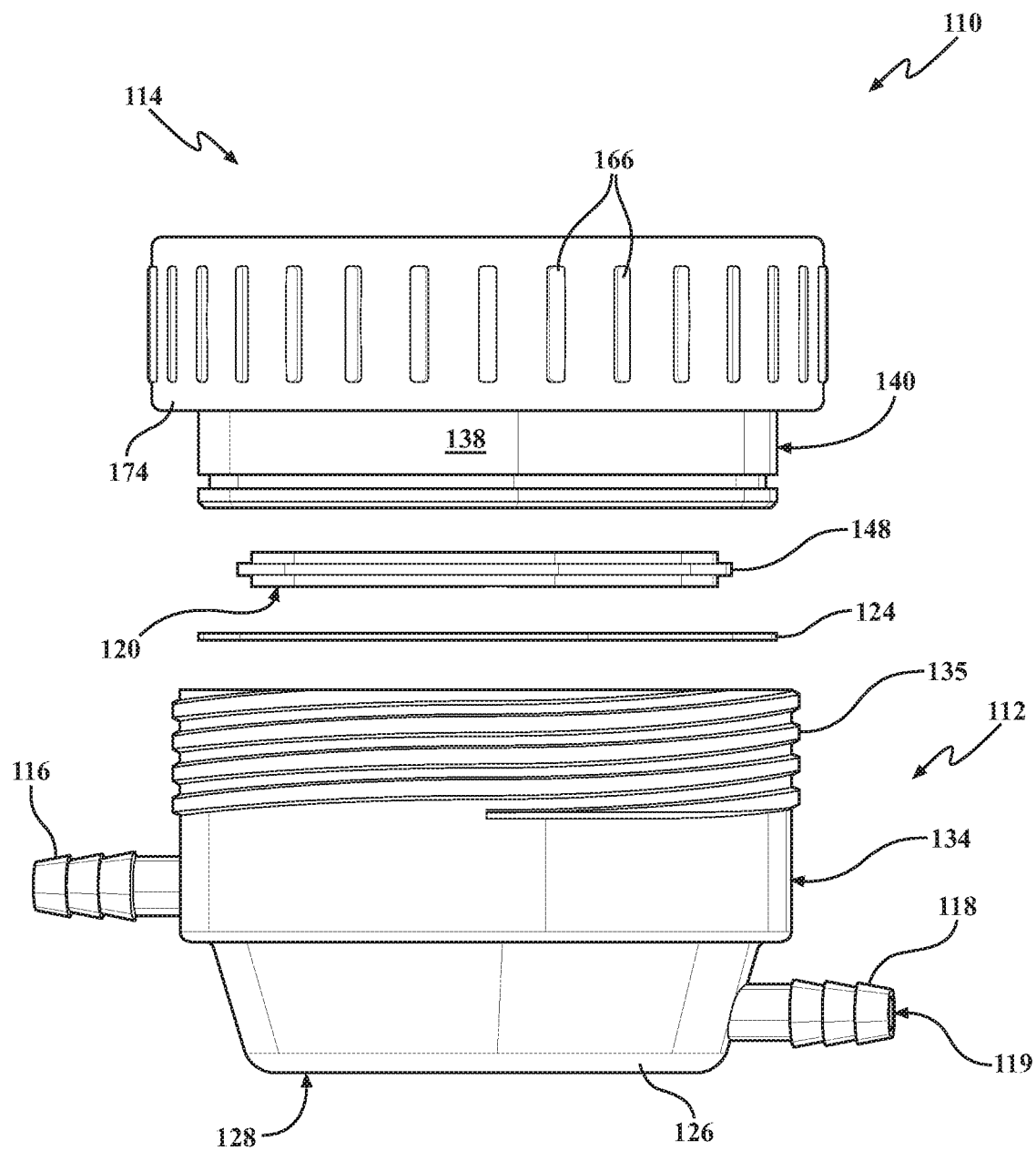
FIG. 15 is an exploded view of the device of FIG. 10 which isolates the compression surface support structure of the press member which defines the compression surface.
Figure 16:
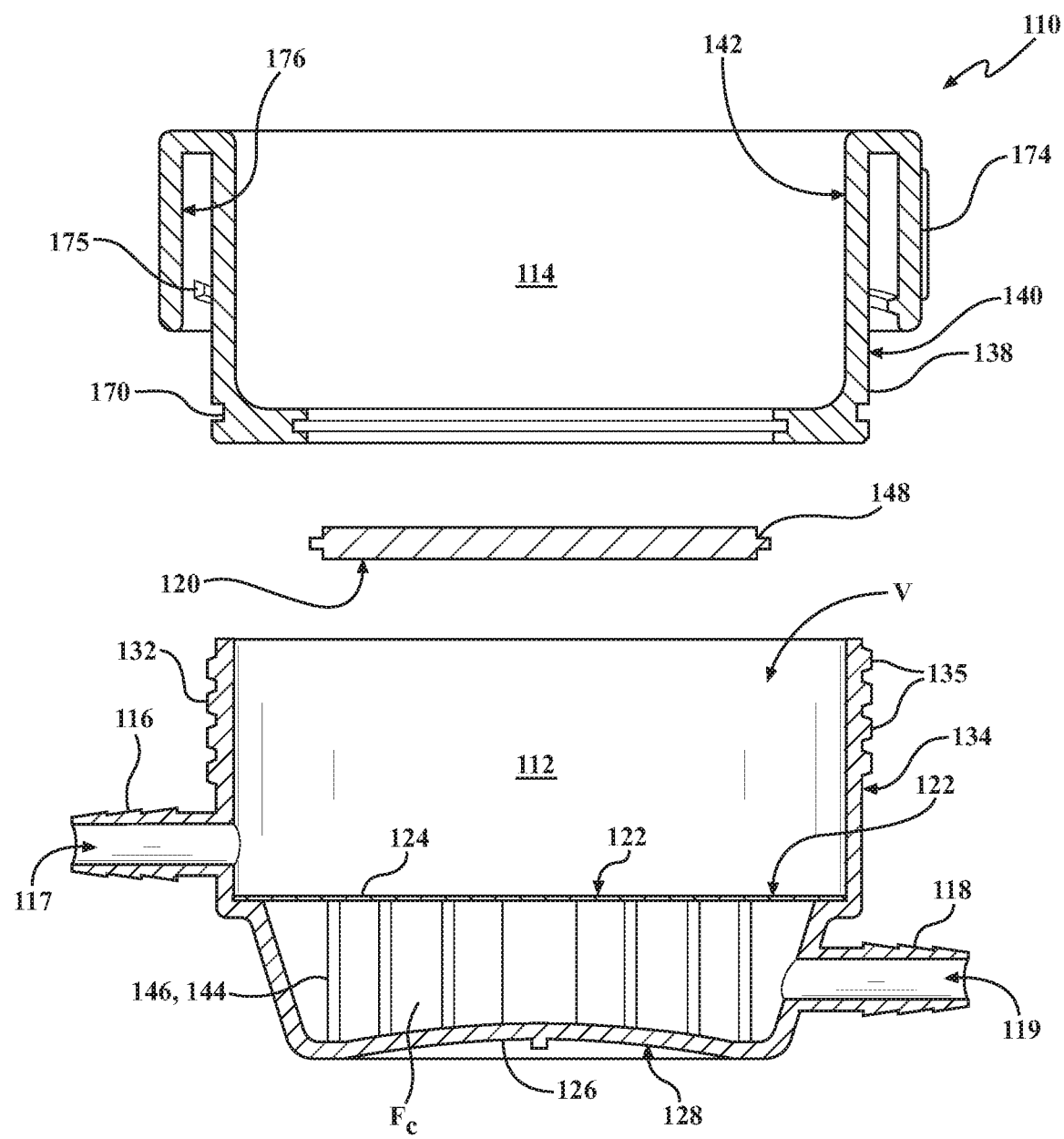
FIG. 16 is a cross-sectional view of the device of FIG. 10 taken along B-B and applied to the exploded view of the device shown in FIG. 15 which isolates the compression surface support structure of the press member which defines the compression surface.

FIG. 15 is an exploded view of the device 110 of FIGS. 10-17A-D which isolates the compression surface support structure 148 of the press member 114 which defines the compression surface 120. It should be appreciated that in various examples, the compression surface 120 is defined by the inner surface 130 of the chamber end 126 (there is no compression surface support structure 148). It should also be appreciated that some examples include the compression surface support structure 148. Finally, it should also be appreciated that, in some examples, independently of what component it is located on, the compression surface 120 is defined by the compliant member 50, 150 in some examples, but in other examples the compression surface 120 need not be defined by the compliant member 50, 150. That is, in some examples, the compression surface 120 could be defined via a thermoplastic or a metal component. FIG. 16 is a cross-sectional view of the device 110 of FIGS. 10-17A-D taken along B-B of FIG. 10 and applied to the exploded view of the device 110 shown in FIG. 15 which isolates the compression surface support structure 148 of the press member 114 which defines the compression surface 120.

Figure 17A:
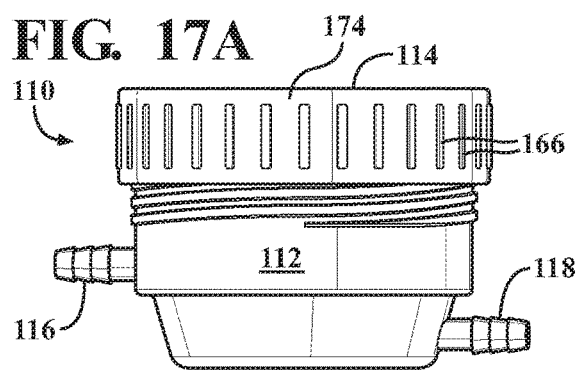
FIGS. 17A through 17D are exemplary schematic illustrations describing use of the example of the device of FIG. 10.
Figure 17B:
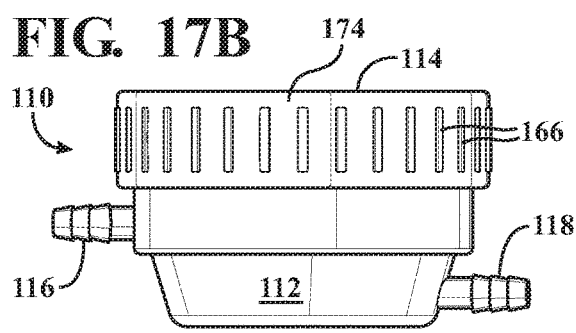
Figure 17C:
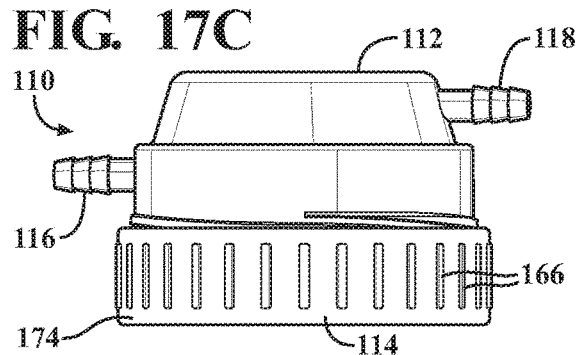
Figure 17D:
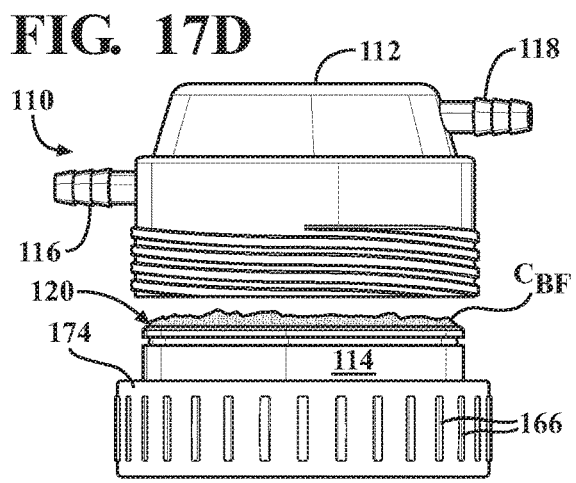

FIGS. 17A through 17D are exemplary schematic illustrations describing use of an example of the device 110 of FIGS. 10-17A-D. In FIG. 17A, the chamber member 112 and the press member 114 are shown rotationally coupled with one another. In FIG. 17A, the composition $C_{BF}$ is acquired through the intake port 116 and collected between the compression surface 120 and the filter support surface 122 with the device 110 in a first orientation. In FIG. 17B, the device 110 is shown after the application of rotational force to the chamber and/or press member 112, 114 in a first direction $RF_{D1}$ moves the compression surface 120 and the filter support surface 122 together to compress the composition $C_{BF}$ therebetween to compact, and further remove filtrate (liquid) from the composition $C_{BF}$. In FIG. 17C, the device 110 is shown "flipped over" or inverted in a second orientation. In FIG. 17D, the device 110 is shown after the application of rotational force to the chamber and/or press member 112, 114 in a second direction $RF_{D2}$, opposite the first direction $RF_{D1}$, to decouple the chamber member 112 and the press member 114, with access to the compacted composition $C_{BF}$ provided (as it sits on the compression surface 120).

The subject disclosure also contemplates examples of the device 110 for collecting and processing bone fragments which is generally described as including the chamber member 112 and the press member 114 operably coupled to define the volume V, a compression component comprising the compliant member 150 which defines the compression surface 120, a filter component which defines the filter support surface 122 or the filter 124, the intake port 116 is configured to receive the composition $C_{BF}$, and the vacuum port 118 is configured to be coupled to a vacuum source. In such examples, the composition $C_{BF}$ is acquired through the intake port 116 and collected within the volume V2, and application of force to the chamber and/or the press member 112, 114 decreases the volume V2 and presses the composition $C_{BF}$ against the compression surface 120, to compact the composition $C_{BF}$ and further remove filtrate from the composition $C_{BF}$ through the filter component. However, in these examples the chamber member 112 and the press member 114 are operably coupled to define the volume V2. As such, the chamber member 112 and the press member 114 can be rotationally coupled or mechanically coupled (e.g. with a plunger). That is, the chamber member 112 and the press member 114 are not necessarily rotationally coupled. These examples are advantageous because they employ the compliant member 150 which is just as described above.

Figure 18:
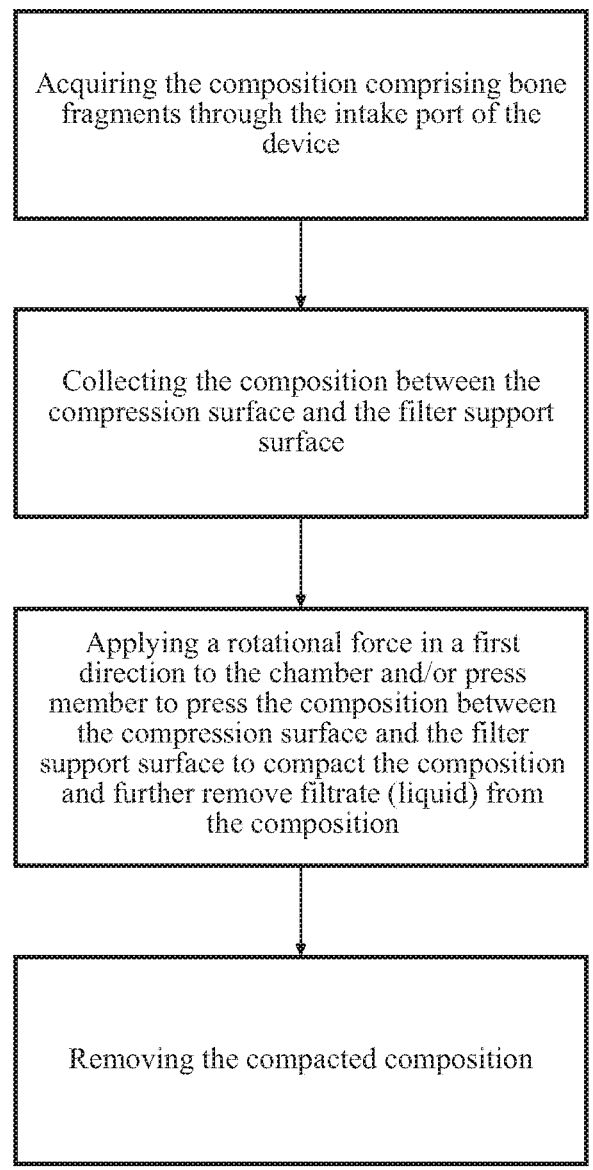
FIG. 18 is a flow diagram generally describing a method of the subject disclosure.

As is alluded above, a method of collecting and processing bone fragments is also disclosed herein. The method comprises the steps of providing a device 10 described above, acquiring the composition $C_{BF}$ through the intake port 16, collecting the composition $C_{BF}$ between the compression surface 20 and the filter support surface 22, applying a rotational force $RF_{D1}$ to the chamber and/or press member 12, 14 to press the composition $C_{BF}$ between the compression surface 20 and the filter support surface 22 to compact the composition $C_{BF}$ and further remove filtrate from the composition $C_{BF}$, and removing the compacted composition $C_{BF}$ from the device 10. The method is generally described in the flow diagram of FIG. 18.

The method may also include the step of applying a rotational force $RF_{D2}$ to the chamber and/or press member 12, 14 in a second direction, opposite the first direction RFD', to move the compression surface 20 and the filter support surface 22 away from one another. Further, the method may include the step of applying a rotational force to the chamber and/or press members 12, 14 in a second direction $RF_{D2}$, opposite the first direction RFD', to decouple the chamber and the press members 12, 14 to provide access to the composition $C_{BF}$ (e.g. for removal).

Figure 19:
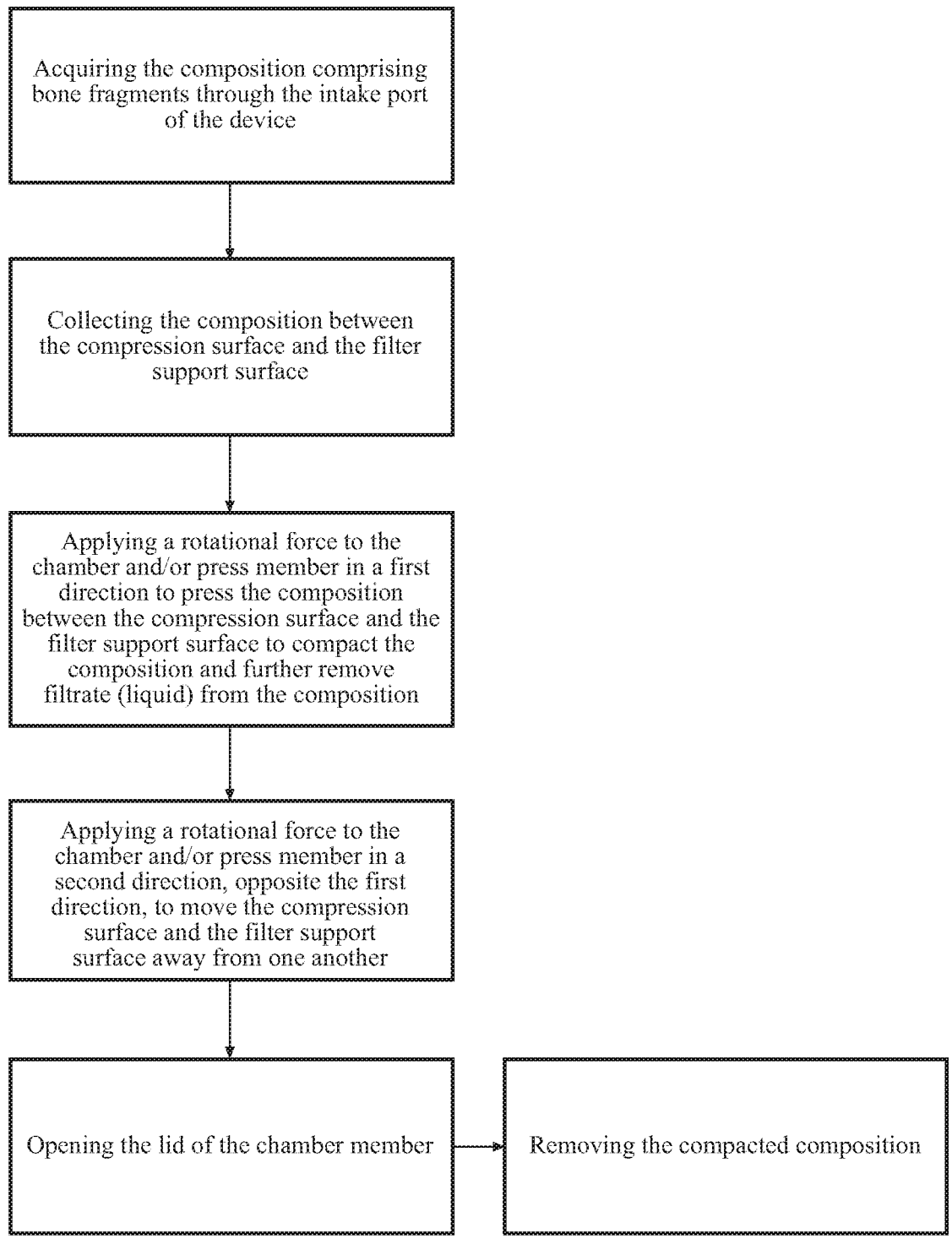
FIG. 19 is a flow diagram describing a particular example of the method of the subject disclosure.
Figure 20:
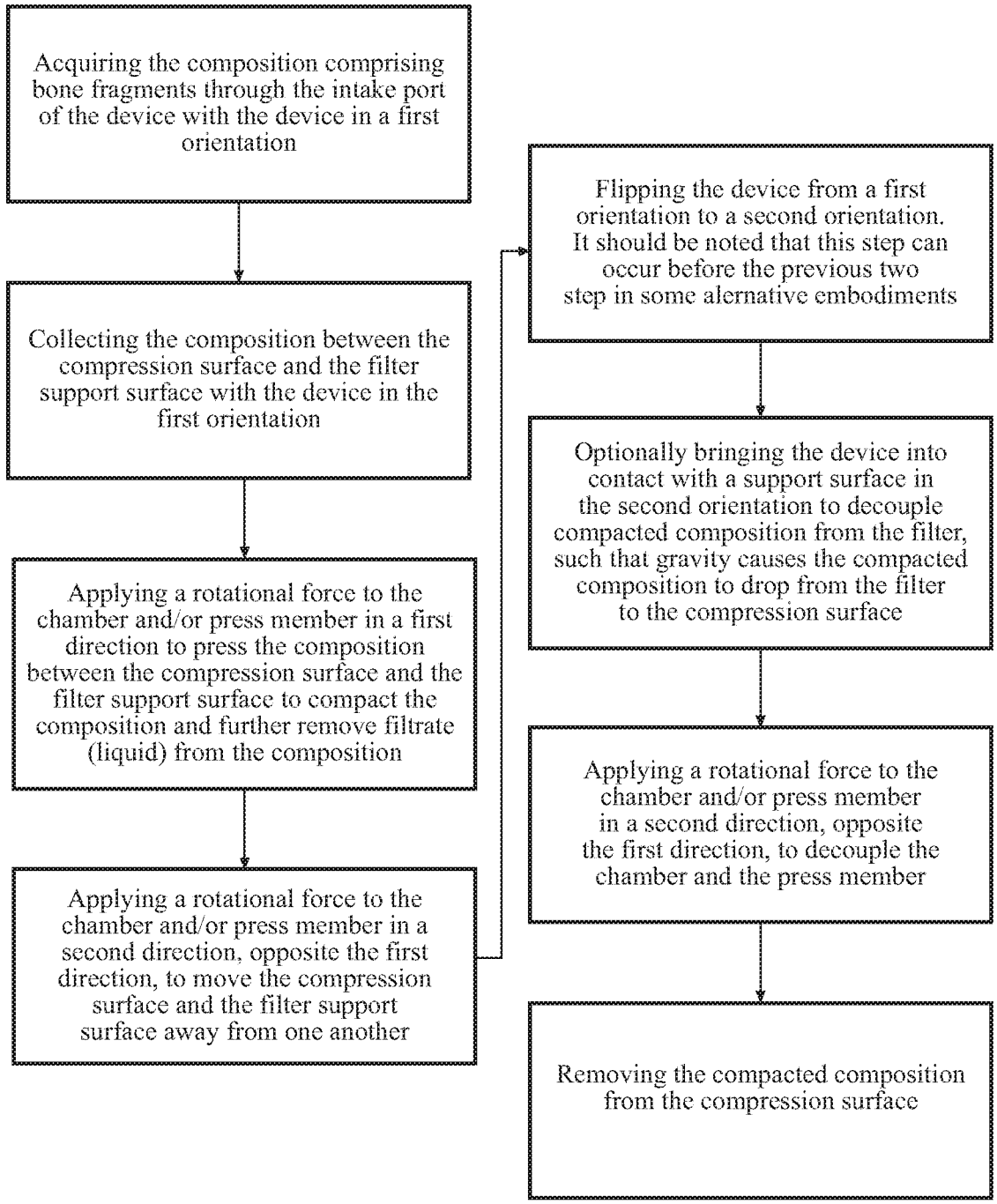
FIG. 20 is a flow diagram describing another example of the method of the subject disclosure including the step of flipping the device from a first to a second orientation during use.

In some examples, the chamber and/or press members 12, 14 do not have to be decoupled to access the composition $C_{BF}$ (e.g. for removal). In these examples, the step of opening the lid (e.g. the chamber end 26 as described above), and subsequently removing the compacted composition $C_{BF}$ is optionally included. An example of the method including the step of opening the lid 26 is described in FIG. 19.

In some examples of the method, such as those described in FIGS. 17A-D and 20, the method may include the steps of acquiring the composition $C_{BF}$ through the intake port 116 and collecting the composition $C_{BF}$ between the compression surface 120 and the filter support surface 122 conducted in a first orientation. Subsequent to the step of collecting, the method of this example includes the step of inverting the device 110 from a first orientation to a second orientation. This example also optionally includes the step of bringing the device 110 into contact with a surface in the second orientation to decouple compacted composition $C_{BF}$ from the filter 124, such that gravity causes the compacted composition $C_{BF}$ to drop from the filter support surface 122 to the compression surface 120. Of course, this method can include the steps of opening the chamber end 26 and/or applying a rotational force to the press member 114 in the second direction $RF_{D2}$, to access and/or remove the compacted composition $C_{BF}$ from the compression surface 120.

Supplemental Disclosure I

In one non-limiting example, a device for collecting and processing bone comprises:
  a chamber member at least partially defining a volume,
  a press member at least partially disposed within the volume;
  a compression surface defined by the chamber and/or press member;
  a filter support surface defined by the chamber and/or press member and configured to support a filter;

an intake port on the chamber and/or press member and configured to receive a composition comprising bone fragments; and a vacuum port on the chamber and/or press member and configured to be coupled to a vacuum source;

wherein the chamber member and the press member are rotationally coupled with one another; and wherein the composition is acquired through the intake port and collected in the volume between the compression surface and the filter support surface, and application of rotational force to the chamber and/or press member in a first direction moves the compression surface and the filter support surface together to compress the composition between the compression surface and the filter support surface to compact and further remove filtrate from the composition.

In some such examples, the application of rotational force to the chamber and/or press members in a second direction, opposite the first direction, moves the compression surface and the filter support surface away from one another.

In some such examples, the application of rotational force to the chamber and/or press members in the second direction allows for decoupling of the chamber member and the press member, and access to the compacted composition for removal.

In some such examples, the chamber member further comprises a compliant member which comprises a compliant material and defines the compression surface.

In some such examples, the compliant material comprises an elastomer.

In some such examples, the compliant material comprises silicone.

In some such examples, the compliant material has a Shore A hardness of from about 30 to about 60 when tested in accordance with ASTM D2240, Standard Test Method for Rubber Property—Durometer Hardness.

In some such examples, the compression surface and the filter support surface are substantially parallel.

In some such examples, the filter support surface is further defined as a removable filter cartridge. In some such examples, the device further comprises a filter having a U.S. Sieve Series mesh size of from about 12 to about 500 (from about 1.7 to about 0.025 mm). The filter may comprise stainless steel.

In some such examples, the chamber member is cylindrical and has a chamber end having an outer surface and an inner surface, and a chamber side wall extending longitudinally from the chamber end and having an outer peripheral surface and an inner peripheral surface. The inner surface can be the compression surface.

In some such examples, the chamber end is operably attached to the side wall, and functions as a lid and allows for access to the composition.

In some such examples, the chamber end is substantially transparent.

In some such examples, the chamber side wall is substantially transparent.

In some such examples, the press member is cylindrical and has a press side wall having an outer peripheral surface.

In some such examples, the chamber or press member further comprises a filter support structure defining a filtrate collection chamber and comprising a plurality of support columns therein, the support structure is configured to support a filter and allow for the collection and removal of filtrate including filtrate which passes through the filter.

In some such examples, the inner peripheral surface of the chamber side wall of the chamber member is shaped to rotatably engage the outer peripheral surface of the side wall of the press member.

In some such examples, the inner peripheral surface of the chamber side wall and the outer peripheral surface of the press side wall are threaded (or are in threaded engagement).

In some such examples, the chamber member includes the intake port and the vacuum port.

In some such examples, the chamber member includes the intake port and the press member includes the vacuum port.

In some such examples, the device includes a snorkel comprising a suction port and a void space, the snorkel being in fluid communication with the vacuum port and configured to remove filtrate from between the compression surface and the filter surface via an alternative fluid communication path.

In some such examples, the device includes an o-ring operatively positioned between the chamber member and the press member.

Supplemental Disclosure II

In some non-limiting examples, a surgical system for use in collecting and processing bone fragments comprises:

a harvesting tool configured to collect bone fragments, the harvesting tool shaped to couple with an intake hose;

a device for collecting and processing bone fragments, the device comprising:

a chamber member at least partially defining a volume, a press member at least partially disposed within the volume;

a compression surface defined by the chamber and/or press member;

a filter support surface defined by the chamber and/or press member and configured to support a filter;

an intake port on the chamber and/or press member and configured to receive a composition comprising bone fragments; and a vacuum port on the chamber and/or press member and configured to be coupled to a vacuum source;

wherein the chamber member and the press member are rotationally coupled with one another; and wherein the composition is acquired through the intake port and collected in the volume between the compression surface and the filter support surface, and the application of rotational force in a first direction to the chamber and/or press member moves the compression surface and the filter support surface together to compress the composition between the compression surface and the filter support surface to compact and further remove filtrate from the composition.

In some such examples, the application of rotational force to the chamber and/or press members in a second direction, opposite the first direction, moves the compression surface and the filter support surface away from one another.

In some such examples, the compression surface comprises an elastomer.

In some such examples, the filter support surface is further defined as a removable filter cartridge.

In some examples, the device further comprising a filter having a U.S. Sieve Series mesh size of from about 12 to about 500 (from about 1.7 to about 0.025 mm).

In some such examples, the chamber member is cylindrical and has a chamber end having an outer surface and an inner surface, and a chamber side wall extending longitudinally from the chamber end and having an outer peripheral surface and an inner peripheral surface; and the press member is cylindrical and has a press end and a press side wall having an outer peripheral surface. In such examples, the inner peripheral surface of the chamber side wall and the outer peripheral surface of the press side wall are threaded (or are in threaded engagement).

In some such examples, at least one of the chamber end and/or the chamber wall is substantially transparent.

In some such examples, the chamber member includes the intake port and the vacuum port.

In some such examples, the device comprises a snorkel configured to remove filtrate from between the compression surface and the filter surface via an alternative fluid communication path.

In some such examples, the device comprises an o-ring operatively positioned between the chamber member and the press member.

Supplemental Disclosure III

In some non-limiting examples a method of collecting and processing bone fragments comprises the steps of:
  providing a device comprising:
    a chamber member at least partially defining a volume,
    a press member at least partially disposed within the volume;
    a compression surface defined by the chamber and/or press member;
    a filter support surface defined by the chamber and/or press member and configured to support a filter;
    an intake port on the chamber and/or press member and configured to receive a composition comprising bone fragments; and
    a vacuum port on the chamber and/or press member and configured to be coupled to a vacuum source;
      wherein the chamber member and the press member are rotationally coupled with one another; and
      wherein the composition is acquired through the intake port and collected in the volume between the compression surface and the filter support surface, and the application of rotational force in a first direction to the chamber and/or press member moves the compression surface and the filter support surface together to compress the composition between the compression surface and the filter support surface to compact and further remove filtrate from the composition;
  acquiring the composition comprising bone fragments through the intake port;
  collecting the composition between the compression surface and the filter support surface;
  applying a rotational force to the chamber and/or press member in a first direction to press the composition between the compression surface and the filter support surface to compact the composition and further remove filtrate from the composition; and
  removing the compacted composition.

In some such examples the step of applying a rotational force to the chamber and/or press member in a second direction, opposite the first direction, to move the compression surface and the filter support surface away from one another.

In some such examples the method further comprises the step of applying a rotational force to the chamber and/or press members in a second direction, opposite the first direction to decouple the chamber and the press members to provide access to the compacted composition.

In some such examples the method further comprises the step of opening a lid to provide access to the compacted composition.

In some such examples, the steps of acquiring the composition comprising bone fragments through the intake port and collecting the composition between the compression surface and the filter support surface are conducted in a first orientation.

In some such examples the method further comprises the step of inverting the device from a first orientation to a second orientation.

In some such examples the method further comprises the step of bringing the device into contact with a support surface in the second orientation to decouple compacted composition from the filter such that the composition collects on the compression surface.

In some such examples the method further comprises the step of applying a rotational force to the press member in a second direction, opposite the first direction to decouple the chamber and the press member, and removing the compacted composition from the compression surface.

In some such examples, the filter support surface is further defined as a removable filter cartridge, and the method further comprises the step of inserting and/or removing the removable filter cartridge from the volume.

Supplemental Disclosure IV

In some non-limiting examples, a device for collecting and processing bone fragments comprises:
  a chamber member and a press member operably coupled to define a volume,
  a compression component comprising a compliant member which defines a compression surface, the compression component movably disposed within the volume,
  an intake port configured to receive a composition comprising bone fragments;
  a vacuum port configured to be coupled to a vacuum source; and
  a filter component;
  wherein the composition is acquired through the intake port and collected within the volume, and application of force to the chamber and/or the press member decreases the volume and presses the composition against the compression surface, to compact the composition and further remove filtrate from the composition through the filter component.

In some such examples, the compliant material comprises an elastomer.

In some such examples, the complaint material comprises silicone.

In some such examples, the compliant material has a Shore A hardness of from about 30 to about 60 when tested in accordance with ASTM D2240, Standard Test Method for Rubber
Property—Durometer Hardness.

In some such examples, the compression surface and the filter support surface are substantially parallel.

In some such examples, the chamber member and the press member are rotationally coupled with one another.

In some such examples, the filter support surface is further defined as a removable filter cartridge.

It will be appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several examples have been discussed in the foregoing description. However, the examples discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

What is claimed is:

1. A device for collecting and processing bone fragments, said device comprising:
a chamber member at least partially defining a volume,
a press member at least partially disposed within said volume;
a compression surface defined by one of said chamber or press member;
a filter support surface defined by the other of said chamber or press member and configured to support a filter;
an intake port configured to receive a composition comprising bone fragments; and
a vacuum port configured to be coupled to a vacuum source;
wherein said chamber member and said press member are rotationally coupled with one another; and
wherein the composition is acquired through said intake port and collected in said volume between said compression surface and said filter support surface, and application of rotational force to said chamber or press member in a first direction moves said compression surface and said filter support surface together to compress the composition between said compression surface and said filter support surface to compact and further remove filtrate from the composition.

2. The device as set forth in claim 1, wherein application of rotational force to said chamber or press members in a second direction, opposite said first direction, moves said compression surface and said filter support surface away from one another.

3. The device as set forth in claim 2, wherein application of rotational force to said chamber or press members in said second direction allows for decoupling of said chamber member and said press member, and access to the compacted composition for removal.

4. The device as set forth in claim 1, wherein said chamber member further comprises a compliant member which comprises a compliant material and defines said compression surface.

5. The device as set forth in claim 1, further comprising a filter having a mesh size of from about 1.7 to about 0.025 mm.

6. The device as set forth in claim 1, wherein said chamber member is cylindrical and has a chamber end having an outer surface and an inner surface, and a chamber side wall extending longitudinally from said chamber end and having an outer peripheral surface and an inner peripheral surface.

7. The device as set forth in claim 6, wherein said inner surface is said compression surface.

8. The device as set forth in claim 7, wherein said chamber end is operably attached to said chamber side wall, and functions as a lid and allows for access to the composition.

9. The device as set forth in claim 8, wherein at least one of said chamber end or said chamber side wall is substantially transparent.

10. The device as set forth in claim 1, wherein said press member is cylindrical and has a press side wall having an outer peripheral surface.

11. The device as set forth in claim 1, wherein said chamber or press member further comprises a filter support structure defining a filtrate collection chamber and comprising a plurality of support columns therein, said support structure configured to support a filter and allow for the collection and removal of filtrate including filtrate which passes through the filter.

12. The device as set forth in claim 1, wherein an inner peripheral surface of a chamber side wall of said chamber member is shaped to rotatably engage an outer peripheral surface of a side wall of said press member.

13. The device as set forth in claim 1, wherein said chamber member includes said intake port and said vacuum port.

14. The device as set forth in claim 1 including a snorkel comprising a suction port and a void space, said snorkel in fluid communication with said vacuum port and configured to remove filtrate from between said compression surface and said filter surface via an alternative fluid communication path.

15. A method of collecting and processing bone fragments, said method comprising the steps of:
providing a device comprising:
a chamber member at least partially defining a volume,
a press member at least partially disposed within the volume;
a compression surface defined by one of the chamber or press member;
a filter support surface defined by the other of the chamber or press member and configured to support a filter;
an intake port configured to receive a composition comprising bone fragments; and
a vacuum port configured to be coupled to a vacuum source;
wherein the chamber member and the press member are rotationally coupled with one another; and
wherein the composition is acquired through the intake port and collected in the volume between the compression surface and the filter support surface;
acquiring the composition comprising bone fragments through the intake port;
collecting the composition between the compression surface and the filter support surface;
applying a rotational force to the chamber or press member in a first direction to move the compression surface and the filter support surface together and press the composition between the compression surface and the filter support surface to compact the composition and remove filtrate from the composition; and
removing the compacted composition.

16. The method as set forth in claim 15, further comprising the step of applying a rotational force to the chamber or press members in a second direction, opposite the first direction to decouple the chamber and the press members to provide access to the compacted composition.

17. The method as set forth in claim 15, wherein the filter support surface is further defined as a removable filter cartridge, and the method further comprises the step of inserting and removing the removable filter cartridge from the volume.

18. A device for collecting and processing bone fragments, said device comprising:
a chamber member and a press member operably coupled to define a volume,
a compression component comprising a compliant member, the compliant member having an elastomer thereon defining a compression surface, said compression component movably disposed within said volume, an intake port configured to receive a composition comprising bone fragments;

a vacuum port configured to be coupled to a vacuum source; and a filter component defining a filter support surface, with the filter support surface substantially parallel with the compression surface;

wherein the composition is acquired through said intake port and collected within said volume between said compression surface and said filter support surface, and application of force to said chamber or said press member decreases said volume and presses the composition against said compression surface, to compact the composition and remove filtrate from the composition through said filter component.

19. The device as set forth in claim 18, wherein said chamber member and said press member are rotationally coupled with one another.

* * * * *